United States Patent
Kronthaler

(10) Patent No.: US 9,107,902 B2
(45) Date of Patent: Aug. 18, 2015

(54) USE OF VWF STABILIZED FVIII PREPARATIONS AND OF VWF PREPARATIONS WITHOUT FVIII FOR EXTRAVASCULAR ADMINISTRATION IN THE THERAPY AND PROPHYLACTIC TREATMENT OF BLEEDING DISORDERS

(75) Inventor: Ulrich Kronthaler, Deisenhofen (DE)

(73) Assignee: CSL BEHRING GMBH, Marburg (DE)

( * ) Notice: Subject to any disclaimer, the term of this patent is extended or adjusted under 35 U.S.C. 154(b) by 1067 days.

(21) Appl. No.: 12/664,005

(22) PCT Filed: Jun. 13, 2008

(86) PCT No.: PCT/EP2008/004770
§ 371 (c)(1),
(2), (4) Date: May 28, 2010

(87) PCT Pub. No.: WO2008/151817
PCT Pub. Date: Dec. 18, 2008

(65) Prior Publication Data
US 2010/0286047 A1 Nov. 11, 2010

(30) Foreign Application Priority Data
Jun. 13, 2007 (EP) .................................... 07011545

(51) Int. Cl.
*A61K 38/36* (2006.01)
*A61K 38/37* (2006.01)
*A61K 38/00* (2006.01)
*A61K 35/16* (2006.01)
*A61K 38/27* (2006.01)

(52) U.S. Cl.
CPC .................. *A61K 38/36* (2013.01); *A61K 38/27* (2013.01)

(58) Field of Classification Search
None
See application file for complete search history.

(56) References Cited

U.S. PATENT DOCUMENTS

| 4,757,006 | A | 7/1988 | Toole et al. |
|---|---|---|---|
| 5,408,039 | A | 4/1995 | Burnouf-Radosevich et al. |
| 5,854,403 | A | 12/1998 | Fischer et al. |
| 7,625,866 | B2 | 12/2009 | Kumpe et al. |
| 2004/0132654 | A1* | 7/2004 | Kumpe et al. .................... 514/12 |
| 2006/0160948 | A1 | 7/2006 | Scheiflinger et al. |
| 2008/0234193 | A1* | 9/2008 | Bossard et al. .................. 514/12 |

FOREIGN PATENT DOCUMENTS

| EP | 0503991 B1 | 9/1998 |
|---|---|---|
| EP | 0784632 B1 | 1/1999 |
| EP | 0772452 B1 | 8/2002 |
| EP | 0871649 B1 | 11/2002 |
| EP | 1258497 A2 | 11/2002 |
| EP | 1258497 A3 | 11/2002 |
| EP | 0710114 B1 | 3/2003 |
| EP | 1405863 A1 | 4/2004 |
| EP | 1 405 863 A1 | 7/2004 |
| EP | 1258497 B1 | 2/2005 |
| JP | 2004 123744 A | 4/2004 |
| JP | 2010 501522 A | 1/2010 |
| WO | WO 95 26750 | 10/1995 |
| WO | WO 2006/071801 A2 | 7/2006 |
| WO | WO 2006/071801 A3 | 7/2006 |

OTHER PUBLICATIONS

Amano K. et al., "Autoantibody to factor VIII that has less reactivity to factor VIII/von Willebrand factor complex," *Am. J. Hematol.*, 49:310-17 (1995).
Bettini R. et al., Review of "Handbook of pharmaceutical excipients, 3rd Ed." by A. Kibbe (ed.), *J. Control. Release*, 71:352-53 (2001).
Bi L. et al., "Targeted disruption of the mouse factor VIII gene produces a model of haemophilia A," *Nat. Genet.*, 10:119-21 (1995).
Bi L. et al., "Further characterization of factor VIII-deficient mice created by gene targeting: RNA and protein studies," *Blood*, 88:3446-50 (1996).
Dalton R.G. et al., "Progress in vWf methodology and its relevance in vWD," in *Factor VIII-von Willebrand Factor* vol. 1 pp. 129-145 (Seghatchian M.J. & Savidge G.F. eds., CRC Press, Inc., Boca Raton, FL).
Dennis C. et al., "A mouse model of severe von Willebrand disease: Defects in hemostasis and thrombosis," *Proc. Natl. Acad. Sci.*, 95:9524-29 (1998).
Ettingshausen C.E. et al., "Recombinant vs. plasma-derived products, especially those with intact VWF, regarding inhibitor development," *Haemophilia*, 12(suppl. 6):106-06 (2006).
Fischer B. et al., "Structural analysis of recombinant von Willebrand factor: identification of hetero- and homo-dimers," *FEBS Lett*, 351:345-48 (1994).
Goudemand J., "Inhibitor development in haemophilia A: the role of von Willebrand factor/factor VIII concentrates," *Haemophilia*, 13(suppl. 5):47-51 (2007).
Kaufman R.J. et al., "Effect of von Willebrand factor coexpression on the synthesis and secretion of factor VIII in Chinese hamster ovary cells," *Mol. Cell. Biol.*, 9(3):1233-42 (1989).
Kaufman R.J., "Expression and structure-function properties of recombinant factor VIII," *Transfus. Med. Rev.*, 6(4):235-46 (1992).
Landskroner K.A. et al., "Thromboelastography measurements of whole blood factor VIII-deficient mice supplemented with rFVIII," *Haemophilia*, 11:346-52 (2005).
Lee G., Review of "Pharmaceutical formulation development of peptides and proteins" by S. Frokjaer et al., *Euro. J. Pharm. and Biopharm.*, 50:329 (2000).
Rizza C.R. et al., "Coagulation assay of VIIC and IXC" in *The Hemophilias* pp. 18-38 (Bloom ed., NY Churchill Livingston) (1992).
Rosén S., "Assay of factor VIII:C with a chromogenic substrate," *J. Haematol.*, 33(suppl. 40):139-45 (1984).

(Continued)

*Primary Examiner* — Jeffrey T Palenik
(74) *Attorney, Agent, or Firm* — Finnegan, Henderson, Farabow, Garrett & Dunner, LLP

(57) ABSTRACT

The present invention relates to the use of von Willebrand Factor (VWF) preparations or of a VWF preparation in combination with coagulation Factor VIII (FVIII) for extravascular administration in the therapy and prophylactic treatment of bleeding disorders.

8 Claims, 16 Drawing Sheets

(56) References Cited

OTHER PUBLICATIONS

Ruggeri Z.M., "Structure and function of von Willebrand factor," *Thromb. Haemost.*, 82(2):576-84 (1999).

European Search Report from the European Patent Office for Application No. EP 12 16 7609, dated Jul. 13, 2012 (8 pages).

Japanese Patent Office Decision of Refusal in JP 2010-511541, dated Feb. 25, 2014.

Amana, K., et al, "Autoantibody to Factor VIII That Has Less Reactivity to Factor VIII/von Willebrand Factor Complex," *Am. J. Hematol.*, vol. 49, pp. 310-317 (1995).

Japanese Search Report in JP 2010-511541, dated Dec. 25, 2012.

U.S. Appl. No. 10/670,563, Amendment after Final, Remarks, and Attachments (Declaration of Gerhardt Kumpe) dated Mar. 14, 2008.

U.S. Appl. No. 10/670,563, Supplemental Amendments and Remarks, dated Jul. 6, 2006.

Notice of Preliminary Rejection, mailed Nov. 25, 2014 in corresponding Korean Patent Appln. No. 10-2009-7025872.

Office Action dated May 8, 2014, issued by the Canadian Intellectual Property Office in Corresponding Canadian Patent Application No. 2,690,218.

\* cited by examiner

Figure 1: Pharmacokinetics of 200 U/kg Monoclate-P® injected i.v. or s.c. (n=2/group; mean +SD)
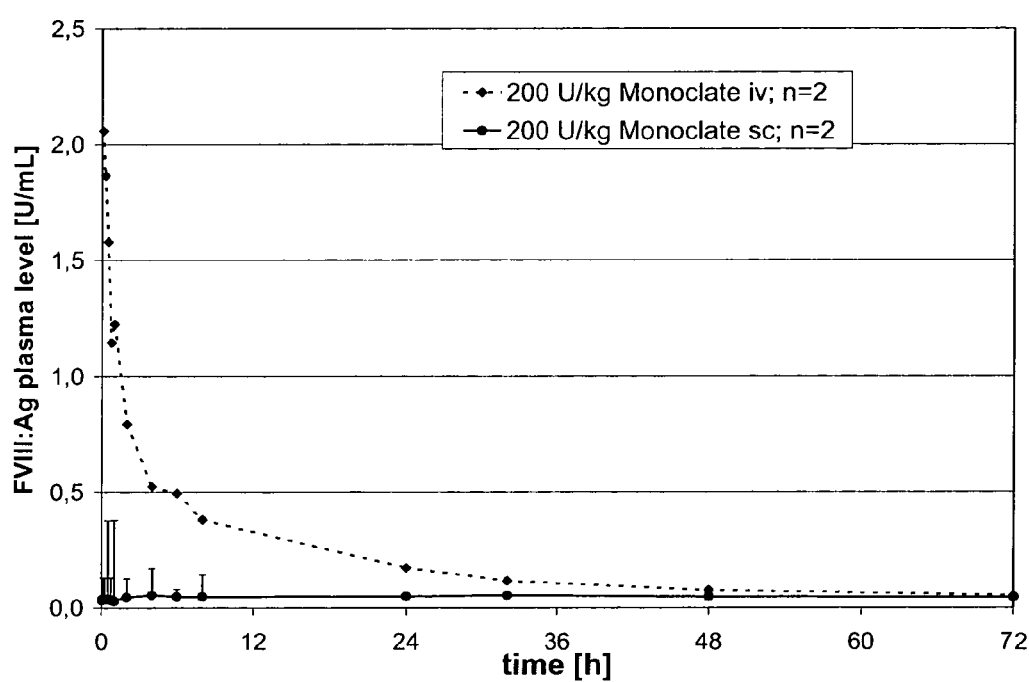

Figure 2: FVIII activity in plasma of FVIII ko mice following 100 U/kg Monoclate-P® i.v. or s.c. and 1800 U/kg s.c.
(mean +SD; n=4-5/timepoint)
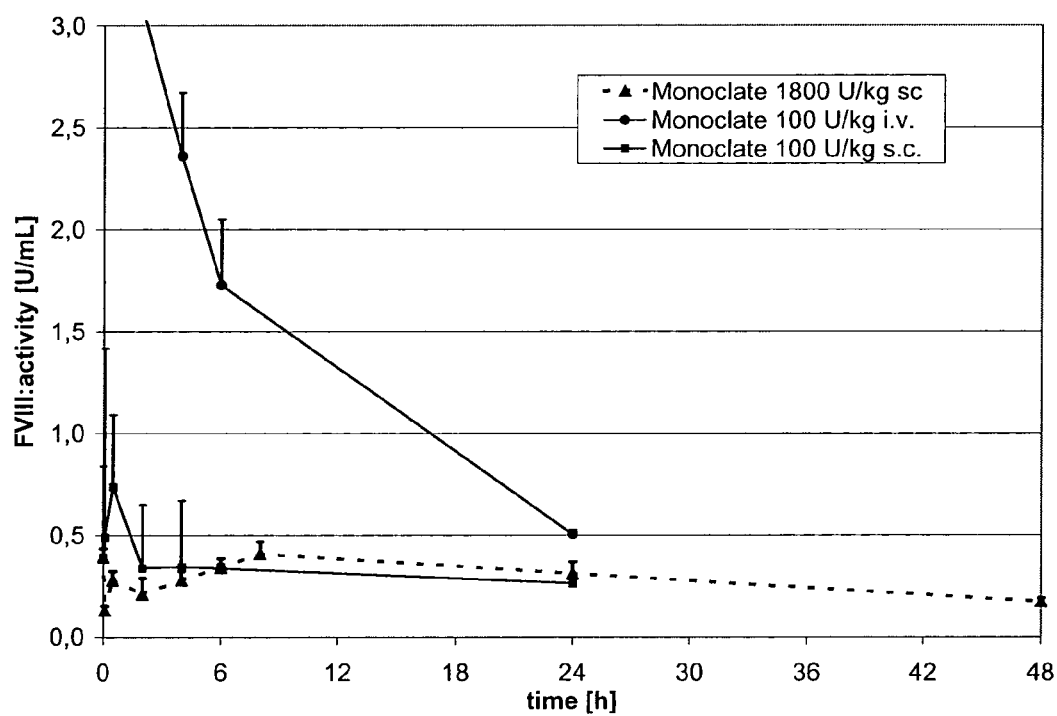

Figure 3: FVIII activity plasma level in FVIII ko mice following 1800 U (FVIII:C)/kg Monoclate-P® or Haemate® P (mean +SD; n=4-5/timepoint)
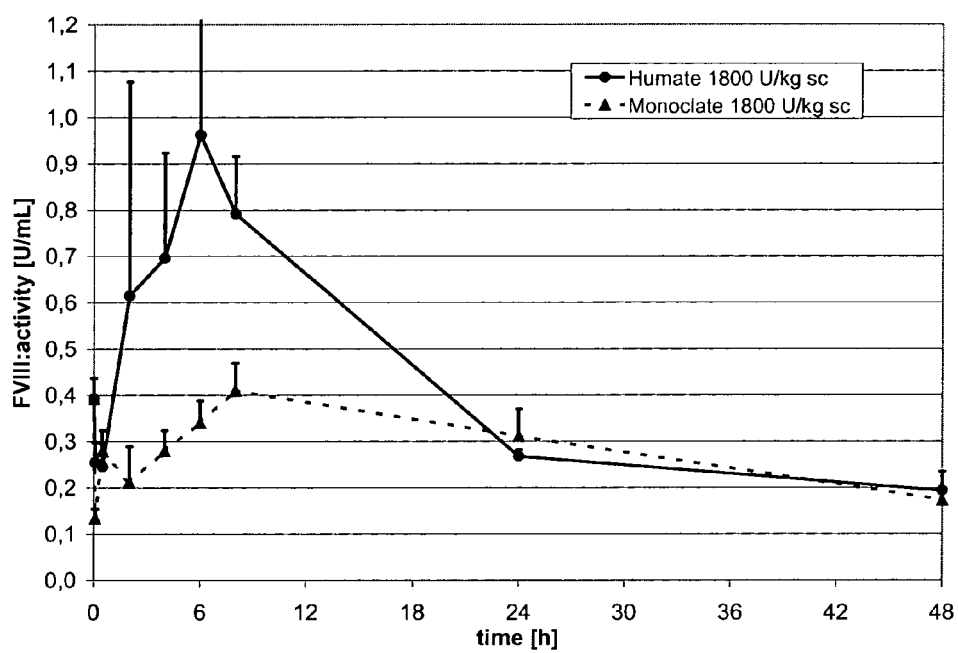

Figure 4: Mean FVIII activity + SD up to 2 days following s.c. injection of 900 or 1800 U (FVIII:C)/kg Haemate® P (n=5/timepoint)
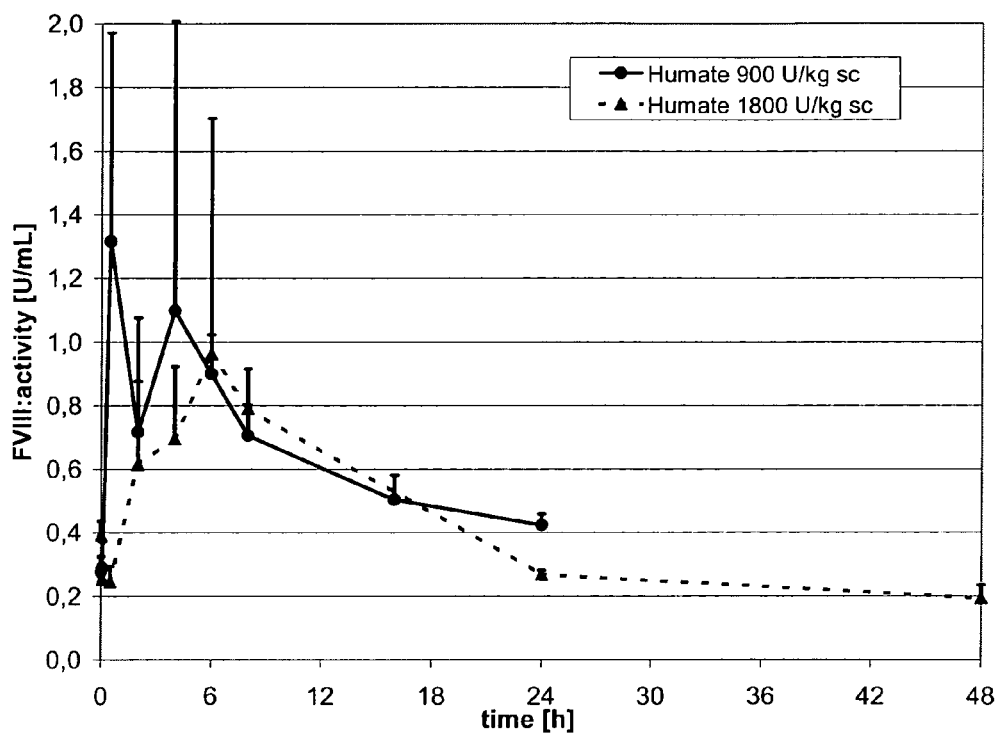

Figure 5: Mean FVIII activity + SD up to 2 days following s.c. injection of 400 U (FVIII:C)/kg Haemate® P, characterized by a varied VWF:Ag/FVIII:C ratio (n=5/timepoint)
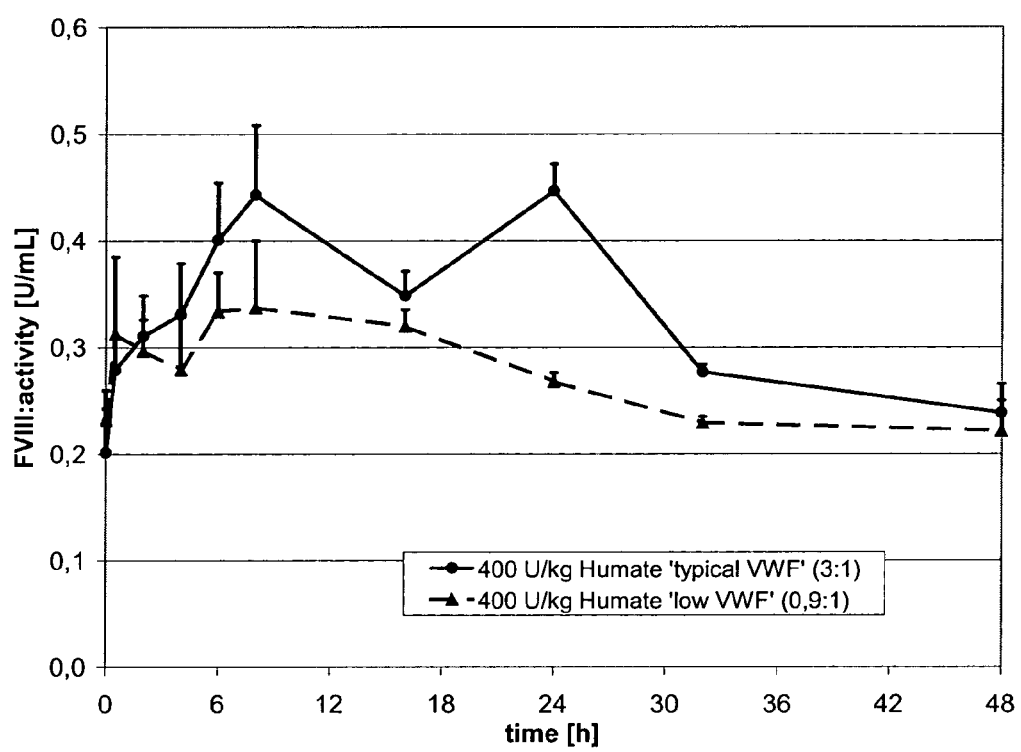

Figure 6: Time course of mean FVIII activity +SD up to 2 days following s.c. injection of 200 U (FVIII:C)/kg Haemate® P, characterized by an increased VWF:Ag/FVIII:C ratio (n=5/timepoint)
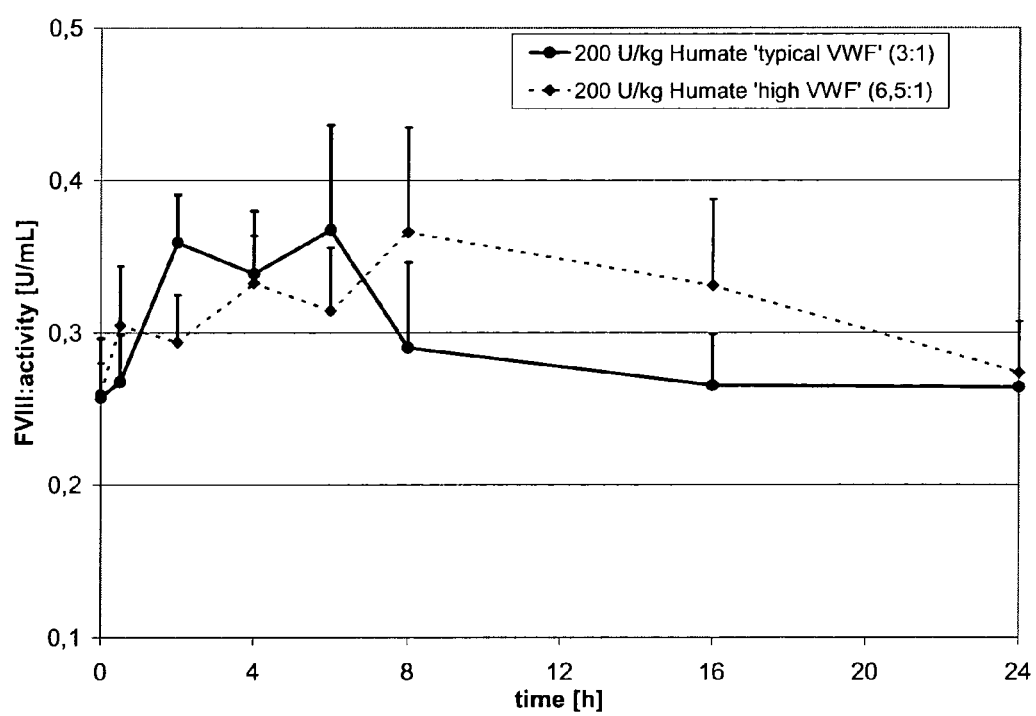

Figure 7: AUDC (FVIII) increase by increased VWF:Ag/FVIII:C ratio
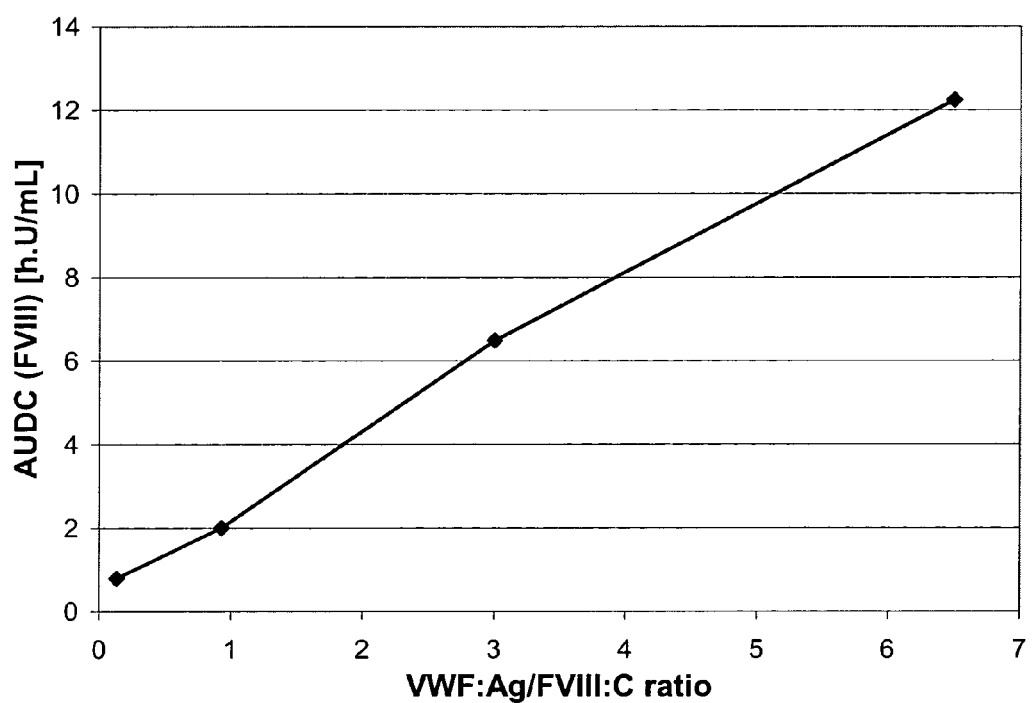

Figure 8: Clot formation time (in TEM) following sc injection of Haemate® P (n=7-24; mean +SD)
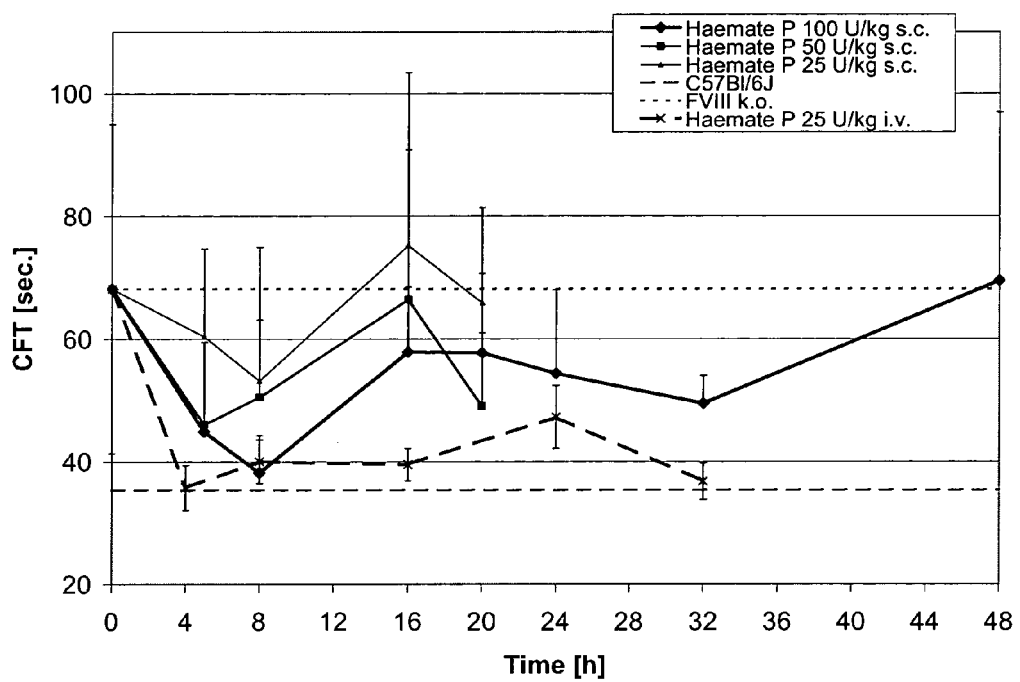

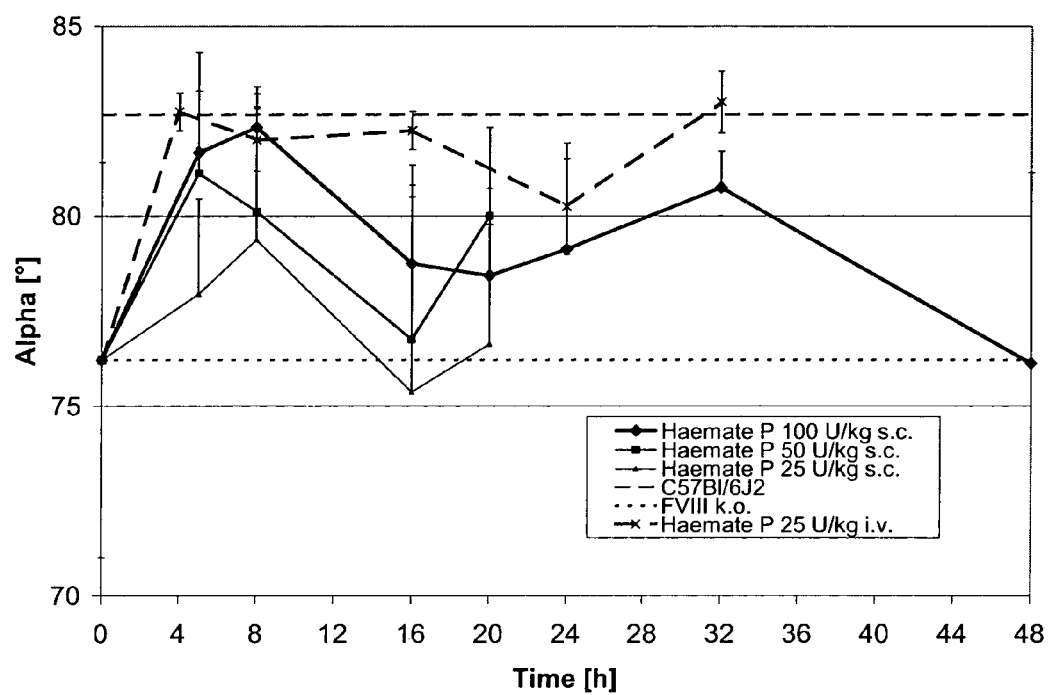
Figure 9: Alpha (in TEM) following sc injection of Haemate® P
(n=7-24; mean +SD)

Figure 10: Comparison of human FVIII:Ag pharmacokinetics in FVIII ko mice following i.v. injection of 100 U (FVIII:C)/kg Haemate® P or Helixate (mean +SD; n=3-5/timepoint)
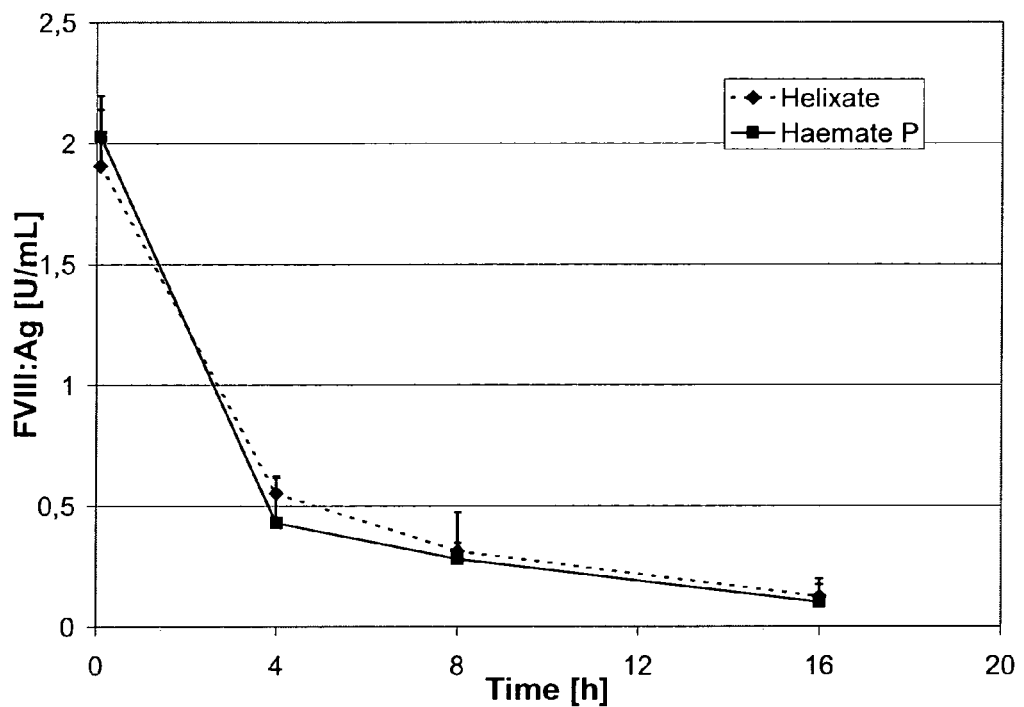

Figure 11: Comparison of human FVIII:Ag pharmacokinetics in VWF ko mice following i.v. injection of 50 U (FVIII:C)/kg Haemate® P and Monoclate P(mean +SD; n=5-6/timepoint)
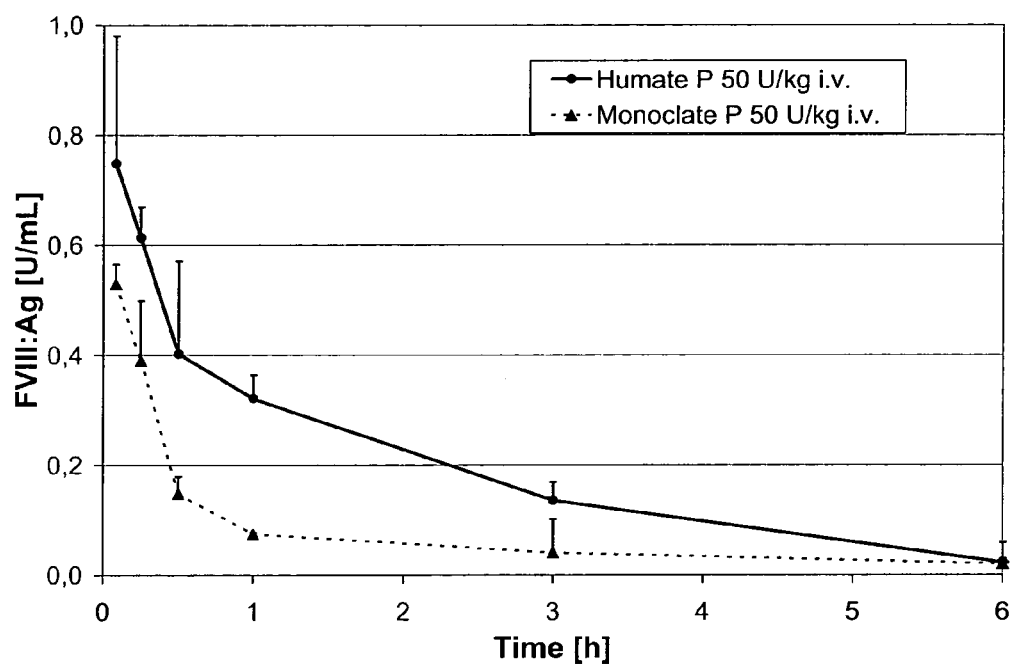

Figure 12: Comparison of FVIII activity in plasma following sc injection of 400 U (FVIII:C)/kg Haemate® P to FVIII ko and VWF ko mice (mean +SD, n=4-5/timepoint
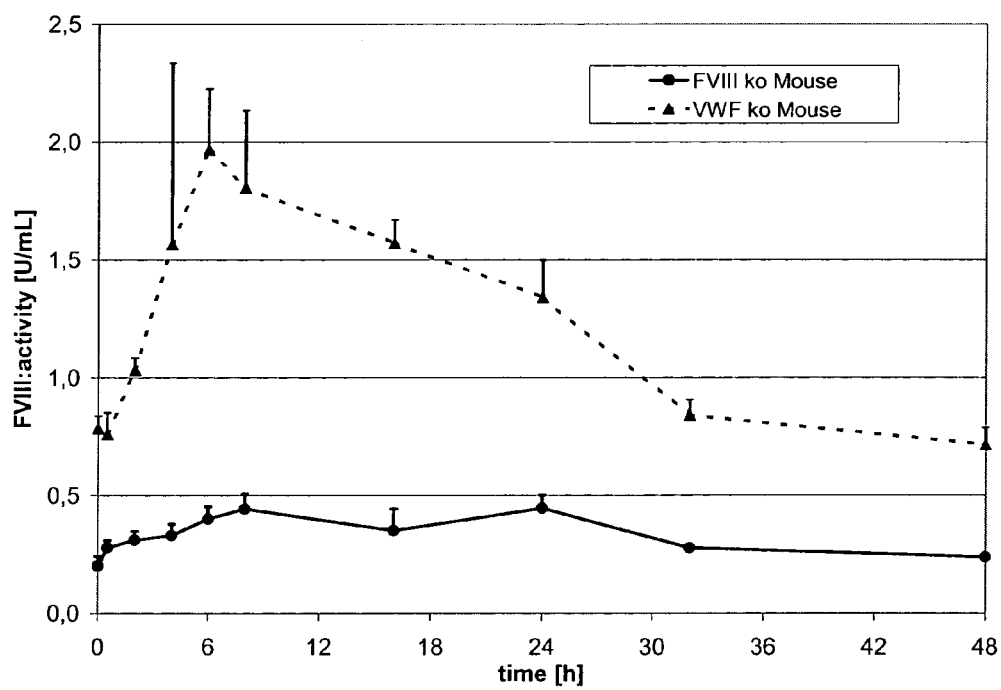

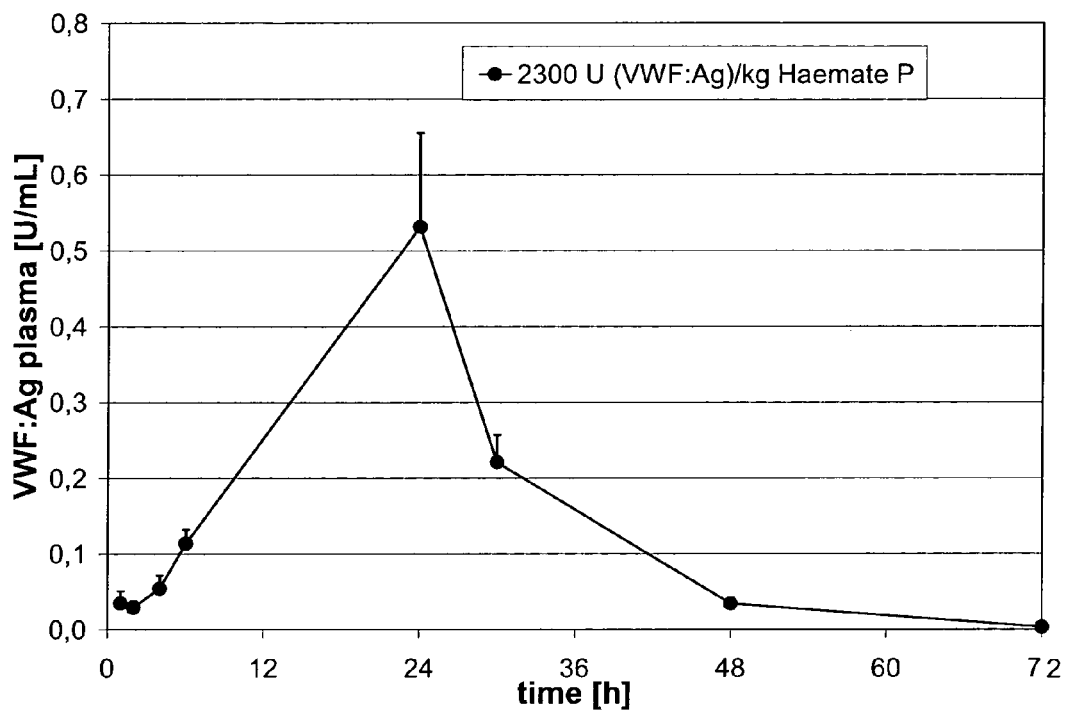
Figure 13: Time course of VWF:Ag following s.c. injection of 2300 U (VWF:Ag)/kg Haemate® P to rabbits (Mean +SD, n=4/timepoint)

Figure 14: Time course of mean VWF:Ag, VWF:RCo and FVIII:C plasma level +SD up to 3 days following s.c. injection of 523 U(VWF:Ag)/kg (n=5/timepoint)
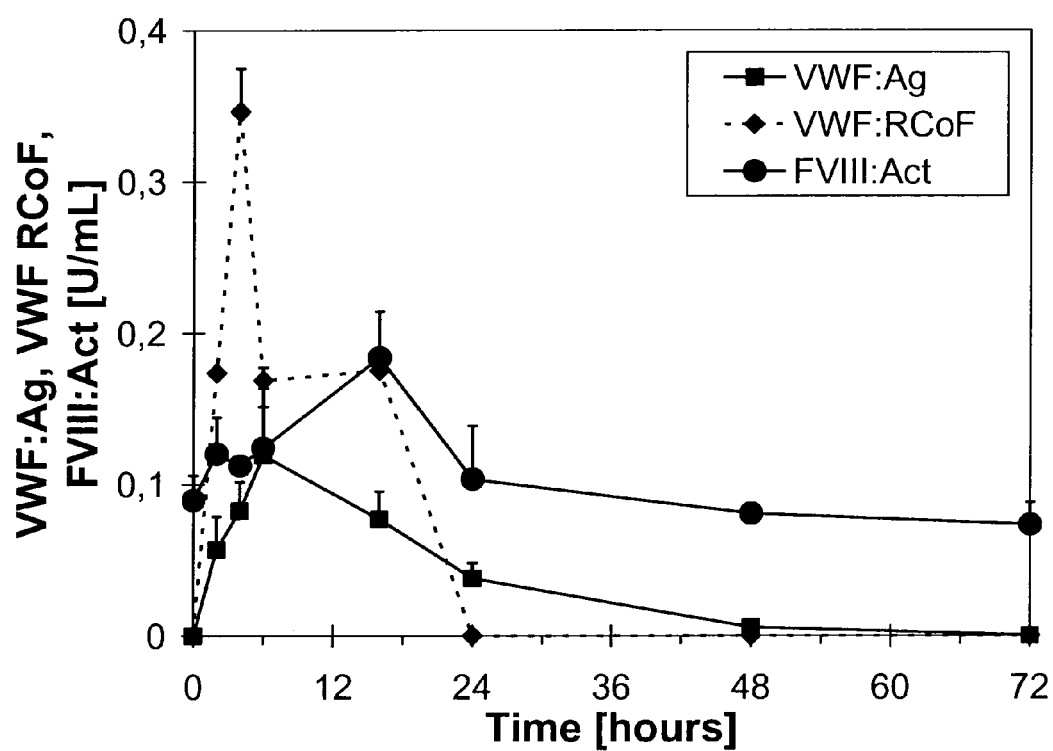

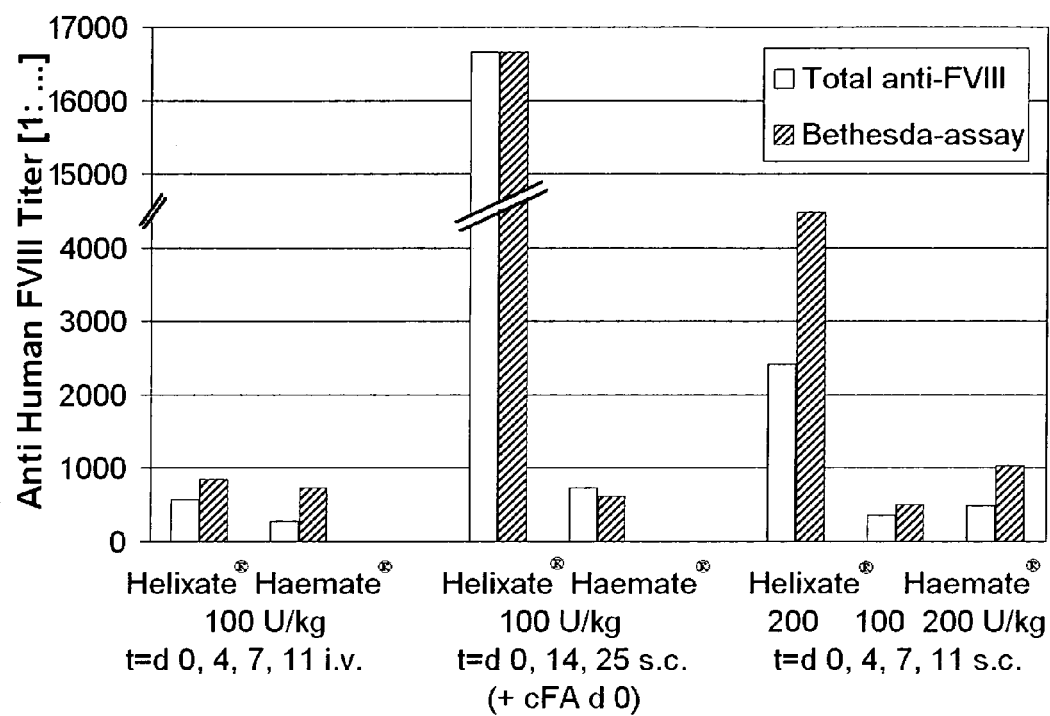
Figure 15: Role of VWF for the generation of anti-FVIII antibodies and FVIII-inhibiting antibodies (Bethesda-assay) following i.v. or s.c. administration of FVIII

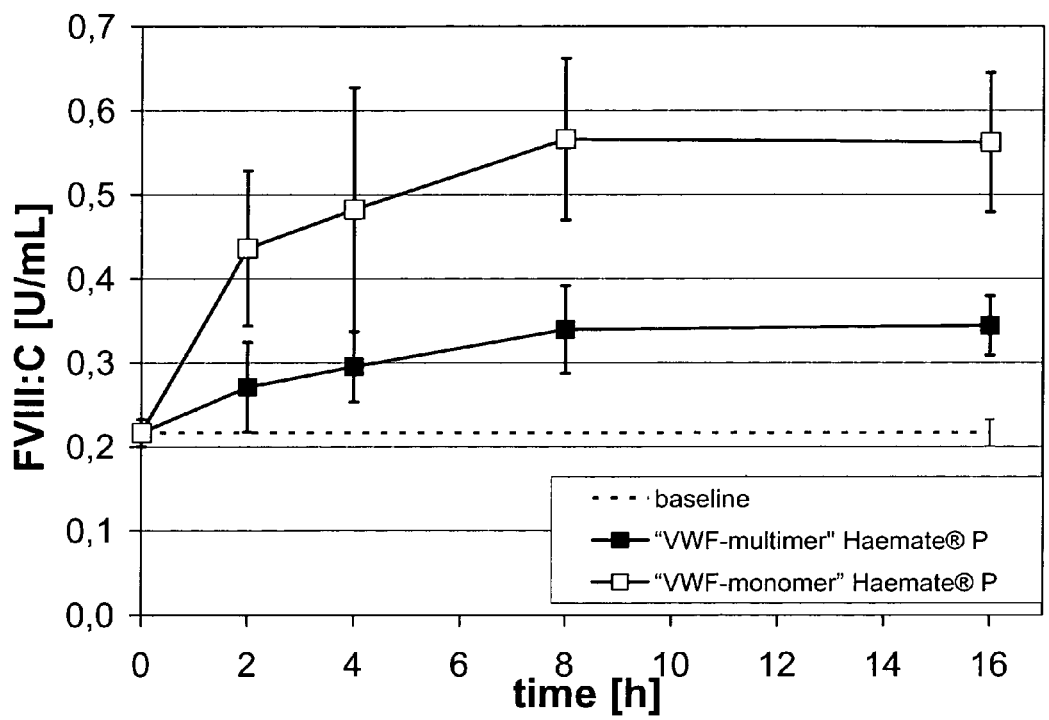
Figure 16: Time course of mean FVIII activity plasma levels ±SD following s.c. injection of 500 U (FVIII:C)/kg Haemate® P preparations, characterized by different VWF:RCo / VWF:Ag ratios (n=4/timepoint)

USE OF VWF STABILIZED FVIII PREPARATIONS AND OF VWF PREPARATIONS WITHOUT FVIII FOR EXTRAVASCULAR ADMINISTRATION IN THE THERAPY AND PROPHYLACTIC TREATMENT OF BLEEDING DISORDERS

FIELD OF THE INVENTION

The present invention relates to the use of von Willebrand Factor (VWF) preparations or of VWF preparation in combination with coagulation Factor VIII (FVIII) for extravascular administration in the therapy and prophylactic treatment of bleeding disorders.

BACKGROUND OF THE INVENTION

VWF is a multimeric adhesive glycoprotein present in the plasma of mammals, which has multiple physiological functions. During primary hemostasis VWF acts as a mediator between specific receptors on the platelet surface and components of the extracellular matrix such as collagen. Via the GP IIbIIIa receptor, VWF also contributes to hemostasis also via promoting platelet-platelet interaction. Moreover, VWF serves as a carrier and stabilizing protein for procoagulant FVIII. VWF is synthesized in endothelial cells and megakaryocytes as a 2813 amino acid precursor molecule. The precursor polypeptide, pre-pro-VWF, consists of a 22-residue signal peptide, a 741-residue pro-peptide and the 2050-residue polypeptide found in mature plasma VWF (Fischer et al., FEBS Lett. 351: 345-348, 1994). Upon secretion into plasma VWF circulates in the form of various species with different molecular sizes. These VWF molecules consist of oligo- and multimers of the mature subunit of 2050 amino acid residues. VWF can be usually found in plasma as one dimer up to multimers consisting of 50-100 dimers (Ruggeri et al. Thromb. Haemost. 82: 576-584, 1999). The in vivo half-life of human VWF in the human circulation is approximately 12 to 20 hours.

The most frequent inherited bleeding disorder in humans is von Willebrand's disease (VWD), which can be treated by replacement therapy with concentrates containing VWF of plasmatic or recombinant origin.

VWF can be prepared from human plasma as for example described in EP 05503991. EP 0784632 describes a method for isolating recombinant VWF.

VWF is known to stabilize FVIII in vivo and, thus, plays a crucial role to regulate plasma levels of FVIII and as a consequence is a central factor to control primary and secondary hemostasis. It is also known that after intravenous administration pharmaceutical preparations containing VWF in VWD patients an increase in endogenous FVIII:C to 1 to 3 units per ml in 24 hours can be observed demonstrating the in vivo stabilizing effect of VWF on FVIII.

FVIII is a blood plasma glycoprotein of about 260 kDa molecular mass, produced in the liver of mammals. It is a critical component of the cascade of coagulation reactions that lead to blood clotting. Within this cascade is a step in which factor IXa (FIXa), in conjunction with FVIII, converts factor X (FX) to an activated form, FXa. FVIII acts as a cofactor at this step, being required with calcium ions and phospholipid for the activity of FIXa. The most common hemophilic disorders is caused by a deficiency of functional FVIII called hemophilia A.

An important advance in the treatment of hemophilia A has been the isolation of cDNA clones encoding the complete 2,351 amino acid sequence of human FVIII (U.S. Pat. No. 4,757,006) and the provision of the human FVIII gene DNA sequence and recombinant methods for its production.

Analysis of the deduced primary amino acid sequence of human FVIII determined from the cloned cDNA indicates that it is a heterodimer processed from a larger precursor polypeptide. The heterodimer consists of a C-terminal light chain of about 80 kDa in a metal ion-dependent association with an about 210 kDa N-terminal heavy chain fragment. (See review by Kaufman, Transfusion Med. Revs. 6:235 (1992)). Physiological activation of the heterodimer occurs through proteolytic cleavage of the protein chains by thrombin. Thrombin cleaves the heavy chain to a 90 kDa protein, and then to 54 kDa and 44 kDa fragments. Thrombin also cleaves the 80 kDa light chain to a 72 kDa protein. It is the latter protein, and the two heavy chain fragments (54 kDa and 44 kDa above), held together by calcium ions, that constitute active FVIII. Inactivation occurs when the 72 kDa and 54 kDa proteins are further cleaved by thrombin, activated protein C or FXa. In plasma, this FVIII complex is stabilized by association with a 50-fold excess of VWF protein ("VWF"), which appears to inhibit proteolytic destruction of FVIII as described above.

The amino acid sequence of FVIII is organized into three structural domains: a triplicated A domain of 330 amino acids, a single B domain of 980 amino acids, and a duplicated C domain of 150 amino acids. The B domain has no homology to other proteins and provides 18 of the 25 potential asparagine(N)-linked glycosylation sites of this protein. The B domain has apparently no function in coagulation and can be deleted with the B-domain deleted FVIII molecule still having procoagulatory activity.

The stabilizing effect of VWF on FVIII has also been used to aid recombinant expression of FVIII in CHO cells (Kaufman et al. 1989, Mol Cell Biol).

Until today the standard treatment of Hemophilia A and VWD involves frequent intravenous infusions of preparations of FVIII and VWF concentrates derived from the plasmas of human donors or in case of FVIII that of pharmaceutical preparations based on recombinant FVIII. While these replacement therapies are generally effective, e.g. in severe hemophilia A patients undergoing prophylactic treatment, Factor VIII has to be administered intravenously (i.v.) about 3 times per week due to the short plasma half life of Factor VIII of about 12 hours. Already if levels of above 1% of the FVIII activity in healthy non-hemophiliacs is reached, e.g. by a raise of FVIII levels by 0.01 U/ml, severe hemophilia A is turned into moderate hemophilia A. In prophylactic therapy dosing regimes are designed such that the trough levels of FVIII activity do not fall below levels of 2-3% of the FVIII activity in healthy non-hemophiliacs. Each i.v. administration is cumbersome, associated with pain and entails the risk of an infection especially as this is mostly done in home treatment by the patients themselves or by the parents of children being diagnosed for hemophilia A. In addition the frequent i.v. injections inevitably result in scar formation, interfering with future infusions. As prophylactic treatment in severe hemophilia is started early in life, with children often being less than 2 years old, it is even more difficult to inject FVIII 3 times per week into the veins of such small patients. For a limited period, implantation of port systems may offer an alternative. Despite the fact that repeated infections may occur and ports can cause inconvenience during physical exercise, they are nevertheless typically considered to be favorable as compared to intravenous injections.

Thus there is a great medical need to obviate the need to infuse VWF or FVIII intravenously.

As FVIII is a very large and labile molecule it exhibits a very low bioavailability due to insufficient absorption and severe degradation, if given subcutaneously, intramuscularly or intradermally, i.e. extravascularly.

EP0710114 discloses that FVIII formulations of a B-domain deleted FVIII in a concentration above 1000 IU/ml are suitable for subcutaneous, intramuscular or intradermal administration, leading to a bioavailability of 5-10% after s.c. administration in monkeys measuring the area under the activity (FVIII:C)-time curve.

EP0772452 discloses that FVIII formulations of a B-domain deleted FVIII in a concentration of at least 500 IU/ml together with an organic additive when administered subcutaneously can lead for more than 6 hours to a FVIII plasma level of at least 1.5% of normal FVIII levels. Using hydrolyzed gelatin or soybean oil emulsion as the organic additive and a B-domain deleted FVIII in a concentration of 1100 IU/ml and a dose of 10000 IU/kg, more than 50% bioavailability as measured as the area under the activity (FVIII:C)-time curve was seen in cynomolgus monkeys.

EP1258497 discloses a bioavailability of 5.3% when a B-domain deleted FVIII (specific activity 15000 IU/mg; dose 2500 IU/kg) was administered subcutaneously, whereas a PEGylated conjugate of FVIII achieved bioavailabilities of 22% and 19% respectively in cynomolgus monkeys.

EP 0871649 and EP1258497 disclose an increase of the bioavailability of a pegylated B-domain deleted FVIII and additionally propose to stabilize VWF and/or a combination of FVIII and VWF by conjugation to enable subcutaneous, intramuscular or intradermal administration to treat hemophilia A or VWD respectively.

WO 2006/071801 teaches the pegylation of VWF which may be administered by injection, such as intravenous, intramuscular, or intraperitoneal injection.

It has now been surprisingly found that, although being an extraordinarily large molecule (VWF multimers range from 1 MDa to 20 MDa) VWF can be taken up into the blood stream when administered extravascularly even without any stabilizing covalent modifications, which can entail an increased risk of immune responses, and that VWF can be used to enhance the uptake of FVIII when co-administered with FVIII non-intravenously.

The present invention thus relates to a composition suitable for extravascular administration in the therapy of von Willebrand disease (VWD) and/or hemophilia A comprising von Willebrand factor (VWF)

The ratio of VWF over FVIII is to be understood in the sense of the invention to be the ratio of VWF antigen units over FVIII activity units.

The VWF antigen (VWF:Ag) can be quantified by various immunologic assays, with the most frequently used are Laurell rocket electrophoresis, electroimmunoassay and enzyme-linked immunosorbent assay (ELISA) [Dalton & Savidge, 1989]. Dalton R G, Savidge G F. Progress in vWf methodology and its relevance in VWD. In: Seghatchian M J & Savidge G F (eds): Factor VIII—von Willebrand Factor, CRC Press, Inc., Boca Raton, Fla. 1989, Vol. I, pp. 129-145. Applying the same standard as reference all these, commercially available, tests, generate essentially identical results.

Factor VIII activity can be determined by a one-stage assay (measuring fibrin formation time in one single reaction step (Rizza et al. 1982. Coagulation assay of FVIII:C and FIXa in Bloom ed. The Hemophilias. NY Churchill Livingston 1992)) or a chromogenic assay (the speed with which an enzyme forms is measured by using the enzyme for the splitting of a chromogenic substrate (S. Rosen, 1984. Scand J Haematol 33: 139-145, suppl.)). Both approaches generate essentially identical findings and are also identically named FVIII:C For both VWF:Ag and FVIII:C one international unit (IU) is defined by the current international standard established by the World Health Organization, with one IU FVIII:C or VWF:Ag is approximately equal to the level of Factor VIII or VWF found in 1.0 mL of fresh-pooled human plasma.

Another embodiment of the invention is the use of a pharmaceutical composition suitable for extravascular administration in the therapy of von Willebrand disease (VWD) and/or hemophilia A comprising von Willebrand factor (VWF) or a pharmaceutical composition comprising FVIII and VWF wherein the ratio of VWF antigen over FVIII activity is larger than 2:1. For the manufacture of a medicament for the treatment of VWD and/or hemophilia A when administered extravascularly.

By way of non-limiting example the ratio of VWF antigen to FVIII activity can be more than 2:1 preferentially more than 3:1, more preferentially more than 5:1, even more preferentially more than 15:1 and most preferably more than 25:1.

Also encompassed by the invention is the use of VWF for the manufacture of a medicament to treat VWD and/or hemophilia A wherein after extravascular co-administration with a pharmaceutical preparation of FVIII either
  a) the time period during which the FVIII activity in plasma is increased by at least 0.01 U/ml after injection is prolonged, preferably by a factor of 3, more preferably by a factor of 5, most preferably by a factor of 10
  or
  b) the maximal concentration of FVIII activity in plasma is increased, preferably by 3 fold, more preferably by 10 fold, most preferably by 20 fold
  or
  c) the area under the data curve (AUDC) of FVIII activity is increased, preferably by 5 fold, more preferably by 15, most preferably by 30 fold.

as compared to the respective parameter when said pharmaceutical composition of FVIII is administered in the same concentration, dose and in the same mode of extravascular administration but without VWF.

Preferentially purified VWF is used. Purified VWF in the sense of the invention encompasses VWF compositions in which VWF:Ag is present in a liquid or if stored lyophilized in the liquid after reconstitution prior to injection at a concentration which is by at least a factor of 20, preferentially by at least a factor of 75, more preferentially by at least a factor of 150 higher as compared to its concentration in plasma. Preferably resuspended cryoprecipitate and other low purity preparations of VWF are not used and the purified VWF is enriched to higher purity than in cryoprecipitate. Preferentially VWF of a purity of more than 1 U VWF:Ag/mg total protein (without added stabilizing proteins), more preferentially VWF of a purity of more than 10 U VWF:Ag/mg total protein (without added stabilizing proteins), even more preferentially VWF of a purity of more than 25 U VWF:Ag/mg total protein (without added stabilizing proteins) is used.

Preferentially purified FVIII is used. Purified FVIII in the sense of the invention encompasses FVIII compositions in which FVIII:C is present in a liquid or if stored lyophilized in the liquid after reconstitution prior to injection by at least a factor of 10, preferentially by at least a factor of 30, more preferentially by at least a factor of 70 as compared to its concentration in plasma. Preferably resuspended cryoprecipitate is not used and the purified FVIII is enriched to higher to higher purity than FVIII in cryoprecipitate. Preferentially FVIII of a specific activity (FVIII:C/mg total protein without added stabilizing proteins) of 1 IU/mg or more preferentially more than 5 IU/mg or even more preferentially more than 10 IU/mg is used.

Preferably the formulation comprising VWF or VWF in combination with FVIII is administered subcutaneously. However all other modes of extravascular administration are encompassed, e.g. intramuscular or intradermal administration.

By way of non-limiting example the concentration of VWF can be equal to or more than 150 U (VWF:Ag)/mL preferentially equal to or more 450 U (VWF:Ag)/mL, most preferentially equal to or more than 1500 U (VWF:Ag)/mL.

A typical dose could be equal to or more than 225 U (VWF:Ag)/kg or equal to or more than 75 U (VWF:Ag)/kg, or equal to or more 15 U (VWF:Ag)/kg.

By way of non-limiting example a typical dose of FVIII activity could be equal to or more than 75 U/kg or equal to or more than 25 U/kg or equal to or more than 5 U/kg.

The source of VWF or FVIII is irrelevant, e.g. it can be derived from human plasma or can be produced recombinantly.

When FVIII is recombinant, it can be either in its full-length form or preferably a deletion derivative thereof. More preferably the deletion derivative is recombinant factor VIII SQ (r-VIII SQ). By deletion derivative is here meant coagulation factor VIII, in which the whole or part of the B-domain is missing. Additionally, the factor VIII molecule, and in particular the r-VIII SQ molecule, can be chemically modified, e.g. by PEGylation, covalently linked carbohydrates or polypeptides, in order to improve the stability of the molecule in vivo.

The invention further relates to polynucleotides encoding a modified VWF or FVIII as described in this application. The term "polynucleotide(s)" generally refers to any polyribonucleotide or polydeoxyribonucleotide that may be unmodified RNA or DNA or modified RNA or DNA. The polynucleotide may be single- or double-stranded DNA, single or double-stranded RNA. As used herein, the term "polynucleotide(s)" also includes DNAs or RNAs that comprise one or more modified bases and/or unusual bases, such as inosine. It will be appreciated that a variety of modifications may be made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells.

The skilled person will understand that, due to the degeneracy of the genetic code, a given polypeptide can be encoded by different polynucleotides. These "variants" are encompassed by this invention.

Preferably, the polynucleotide of the invention is a purified polynucleotide. The term "purified" polynucleotide refers to a polynucleotide that is substantially free from other nucleic acid sequences, such as and not limited to other chromosomal and extra-chromosomal DNA and RNA. Purified polynucleotides may be purified from a host cell. Conventional nucleic acid purification methods known to skilled artisans may be used to obtain purified polynucleotides. The term also includes recombinant polynucleotides and chemically synthesized polynucleotides.

Yet another aspect of the invention is a plasmid or vector comprising a polynucleotide according to the invention. Preferably, the plasmid or vector is an expression vector. In a particular embodiment, the vector is a transfer vector for use in human gene therapy.

Still another aspect of the invention is a host cell comprising a polynucleotide of the invention or a plasmid or vector of the invention.

The host cells of the invention may be employed in a method of producing recombinant VWF and/or recombinant FVIII, which is part of this invention. The method comprises:
a) culturing host cells of the invention under conditions such that the VWF and/or FVIII is expressed; and
b) optionally recovering VWF and/or FVIII from the host cells or from the culture medium.

Degree and location of glycosylation or other post-translation modifications may vary depending on the chosen host cells and the nature of the host cellular environment. When referring to specific amino acid sequences, posttranslational modifications of such sequences are encompassed in this application.

"FVIII" as used in this application means a product consisting of the nonactivated form (FVIII). "FVIII" and "VWF" as used in this invention include proteins that have the amino acid sequence of native human FVIII and VWF respectively. It also includes proteins with a slightly modified amino acid sequence, for instance, a modified N-terminal end including N-terminal amino acid deletions or additions so long as those proteins substantially retain the activity of FVIII or VWF respectively. "FVIII" and "VWF" within the above definition also include natural allelic variations that may exist and occur from one individual to another. "FVIII" or "VWF" within the above definition further include variants of FVIII or VWF. Such variants differ in one or more amino acid residues from the wild type sequence. Examples of such differences may include truncation of the N- and/or C-terminus by one or more amino acid residues (e.g. 1 to 10 amino acid residues), or addition of one or more extra residues at the N- and/or C-terminus, e.g. addition of a methionine residue at the N-terminus, as well as conservative amino acid substitutions, i.e. substitutions performed within groups of amino acids with similar characteristics, e.g. (1) small amino acids, (2) acidic amino acids, (3) polar amino acids, (4) basic amino acids, (5) hydrophobic amino acids, (6) aromatic amino acids. Examples of such conservative substitutions are shown in the following table.

TABLE 1

| (1) | Alanine | Glycine | | |
| (2) | Aspartic acid | Glutamic acid | | |
| (3a) | Asparagine | Glutamine | | |
| (3b) | Serine | Threonine | | |
| (4) | Arginine | Histidine | Lysine | |
| (5) | Isoleucine | Leucine | Methionine | Valine |
| (6) | Phenylalanine | Tyrosine | Tryptophane | |

The term "recombinant" means, for example, that the variant has been produced in a host organism by genetic engineering techniques. The FVIII or VWF variant of this invention is usually a recombinant variant.

Expression of the Proposed Variants:

The production of recombinant proteins at high levels in suitable host cells, requires the assembly of the above-mentioned modified cDNAs into efficient transcriptional units together with suitable regulatory elements in a recombinant expression vector, that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The cDNAs are then integrated into the genome of a suitable host cell line for expression of FVIII or VWF. Preferably this cell line should be an animal cell-line of vertebrate origin in order to ensure correct folding, Gla-domain synthesis, disulfide bond formation, asparagine-linked glycosylation, O-linked glycosylation, and other post-translational modifications as well as secretion into the cultivation medium. Examples of other post-translational modifications are hydroxylation and proteolytic processing of the nascent polypeptide chain. Examples of cell lines that can be used are monkey COS-cells, mouse L-cells, mouse C127-cells, hamster BHK-21 cells, human embryonic kidney 293 cells, and hamster CHO-cells.

The recombinant expression vector encoding the corresponding cDNAs can be introduced into an animal cell line in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNAs can also be introduced into animal cells together with another recombinant gene, which may function as a dominant selectable marker in these cells in order to facilitate the isolation of specific cell clones, which have integrated the recombinant DNA into their genome. Examples of this type of dominant selectable marker genes are Tn5 amino glycoside phosphotransferase, conferring resistance to geneticin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated into the genome of the host cell, frequently resulting in a tight physical linkage between the different transcription units.

Other types of selectable marker genes, which can be used together with the cDNA of the desired protein, are based on various transcription units encoding dihydrofolate reductase (dhfr). After introduction of this type of gene into cells lacking endogenous dhfr-activity, preferentially CHO-cells (DUKX-B11, DG-44) it will enable these to grow in media lacking nucleosides. An example of such a medium is Ham's F12 without hypoxanthine, thymidin, and glycine. These dhfr-genes can be introduced together with the coagulation factor cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a bath culture or as a perfusion culture with continuous production of conditioned medium over extended periods of time. Thus, according to the present invention, the above cell lines are well suited for the development of an industrial process for the production of the desired recombinant proteins.

The recombinant protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant protein to a monoclonal antibody, which is immobilised on a solid support. After desorption, the protein can be further purified by a variety of chromatographic techniques based on the above properties.

It is preferred to purify the biologically active FVIII or VWF of the present invention to ≥80% purity, more preferably ≥95% purity, and particularly preferred is a pharmaceutically pure state that is greater than 99.9% pure with respect to contaminating macromolecules, particularly other proteins and nucleic acids, and free of infectious and pyrogenic agents. Preferably, an isolated or purified biologically active FVIII or VWF of the invention is substantially free of other polypeptides except when a combination of FVIII and VWF should be administered.

The recombinant proteins described in this invention can be formulated into pharmaceutical preparations for therapeutic use. The purified proteins may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", $3^{rd}$ edition, Kibbe et al., Pharmaceutical Press (2000)). In particular, the pharmaceutical composition comprising the polypeptide variant of the invention may be formulated in lyophilized or stable soluble form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of non-intravenous administration. Various delivery systems are known and can be used to administer the composition by any convenient route. Preferentially the compositions of the invention are formulated for subcutaneous, intramuscular, intraperitoneal, intracerebral, intrapulmonar, intranasal or transdermal administration, most preferably for subcutaneous, intramuscular or transdermal administration according to conventional methods. The formulations can be administered continuously by infusion or by bolus injection. Some formulations encompass slow release systems.

The modified biologically active FVIII and VWF polypeptides of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

The pharmaceutical composition of the invention may be administered alone or in conjunction with other therapeutic agents. These agents may be incorporated as part of the same pharmaceutical.

Another aspect of the invention is the use of a VWF or a VWF combined with FVIII as described herein, of a polynucleotide of the invention, of a plasmid or vector of the invention, or of a host cell of the invention for the manufacture of a medicament for the treatment or prevention of a blood coagulation disorder. Blood coagulation disorders include but are not limited to hemophilia A and VWD, or FVII/FVIIa deficiency. Preferably these diseases are caused or congenital forms are aggravated by autoimmune antibodies against the respective coagulation factors. In a specific embodiment, the patients to be treated have inhibitor antibodies against factor VIII. Preferably, the treatment comprises human gene therapy.

The mode of administration is preferentially subcutaneous, but encompasses all extravascular routes of administration. This means that superficial administrations, i.e. non vascular as opposed to intravascular injections, would be most preferable to the patient. Most superficial administrations would be administration via epithelial surfaces (on the skin). Of special clinical utility would be an application via a patch. This topical administration requires uptake through the skin, which can be however quite marked, not only with superficial abrasions but also intact skin, and it may include eye drops and nasal applications. Administration via epithelial surfaces includes inhalation, which is suitable due to the extraordinary large surface covered with the protein, leading to rapid uptake and bypassing of the liver. Administration on epithelial surfaces includes dosage forms which are held in the mouth or under the tongue, i.e. are buccal or sublingual dosage forms, possibly even as chewing gum. Since the pH in the mouth is relatively neutral (as opposed to the acidic stomach milieu) this would be positive for a labile protein such as FVIII. Vaginal and even rectal administration might also be considered as some of the veins draining the rectum lead directly to the general circulation. Typically this is most helpful for patients who cannot take substances via the oral route, such as young children.

Intradermal injection (in the skin) would be a more invasive mode of administration, but still suitable for a treatment without assistance or even execution by trained personnel. Intradermal administration would be followed by subcutaneous injection (just under the skin). Typically uptake is quite substantial and can be increased by warming or massaging the injection area. Alternatively vasoconstriction can be achieved, resulting in the opposite behaviour, i.e. reducing the adsorption but prolonging the effect.

Even more invasive extravascular administration includes intramuscular delivery (into the body of the muscle). This might provide benefits by circumventing adipose tissue, but it is typically more painful that subcutaneous injections and especially with patients characterized by a deficient coagulation system, to be improved by the injection, there is the risk of tissue lesions, resulting in bleedings.

Independent of the degree of invasiveness, the VWF:FVIII complex might be loaded to biologically degradable particles, which can be designed to having a high affinity to epithelial surfaces and loaded with the VWF:FVIII complex in order to improve adsorption.

The invention also concerns a method of treating an individual suffering from a blood coagulation disorder such as hemophilia A or FVII/FVIIa deficiency, preferably these diseases are caused by or congenital forms are aggravated by autoimmune antibodies against the respective coagulation factors. The method comprises administering to said individual an efficient amount pharmaceutical composition comprising VWF or VWF in combination with FVIII as described herein. In another embodiment, the method comprises administering to the individual an efficient amount of the polynucleotide of the invention or of a plasmid or vector of the invention. Alternatively, the method may comprise administering to the individual an efficient amount of the host cells of the invention described herein.

One of the major problems in the therapy of hemophilia A is the development of neutralizing antibodies against FVIII. About 25% of these patients develop inhibitory antibodies, neutralizing the activity of FVIII. Accordingly FVIII substitution does not help any more to correct the patients' hemostasis. While such inhibitory antibodies typically are generated by the first couple of treatments, it is currently very difficult to predict which patients will suffer from this complication. Whether the particular FVIII concentrate used plays a role in this is a topic of controversial discussion in the scientific literature. From other proteins, designed to achieve a maximal immune response it is at least clear, that the application mode plays a crucial role, i.e. i.v. injections are typically less immunogenic than s.c. injections. However it was surprisingly found that if FVIII is formulated with VWF even if administered s.c. this formulation generates in hemophilia A mice less inhibitory antibodies than FVIII administered i.v. and certainly less inhibitory antibodies than an s.c. administration of FVIII.

Therefore another embodiment of the invention is the use of VWF for the manufacture of a medicament to treat VWD and/or hemophilia A wherein after extravascular co-administration with a pharmaceutical preparation of FVIII, less inhibitory antibodies against FVIII are generated as compared to when said pharmaceutical composition of FVIII is administered in the same concentration, dose and in the same mode of extravascular administration but without VWF.

For i.v. administration of FVIII there is an ongoing discussion in the scientific literature whether a formulation of FVIII with VWF might decrease the risk for the generation of inhibitory antibodies against FVIII. Our data (Example 10) point to a reduction in the generation of inhibitory antibodies against FVIII when a VWF formulated FVIII is administered.

In a preferred embodiment of the invention at least 15% less inhibitory antibodies are generated when a VWF preparation is extravascularly co-administered with a pharmaceutical preparation of FVIII, as compared to when said pharmaceutical composition of FVIII is administered in the same concentration, dose and in the same mode of extravascular administration but without VWF and wherein the titer of inhibitory antibodies is determined with the Bethesda assay (Goudemand J., Haemophilia, Vol. 13 Suppl. 5: 47-51, 2007; Ettingshausen C. E., Kreuz W., Haemophilia, Vol. 12 Suppl. 6: 102-106, 2006).

Preferably at least 25% less inhibitory antibodies are generated when a VWF preparation is extravascularly co-administered with a pharmaceutical preparation of FVIII, as compared to when said pharmaceutical composition of FVIII is administered in the same concentration, dose and in the same mode of extravascular administration but without VWF and wherein the titer of inhibitory antibodies is determined with the Bethesda assay (Goudemand J., Haemophilia, Vol. 13 Suppl. 5: 47-51, 2007; Ettingshausen C. E., Kreuz W., Haemophilia, Vol. 12 Suppl. 6: 102-106, 2006).

More preferably at least 50% less inhibitory antibodies are generated when a VWF preparation is extravascularly co-administered with a pharmaceutical preparation of FVIII, as compared to when said pharmaceutical composition of FVIII is administered in the same concentration, dose and in the same mode of extravascular administration but without VWF and wherein the titer of inhibitory antibodies is determined with the Bethesda assay.

Most preferably at least 75% less inhibitory antibodies are generated when a VWF preparation is extravascularly co-administered with a pharmaceutical preparation of FVIII, as compared to when said pharmaceutical composition of FVIII is administered in the same concentration, dose and in the same mode of extravascular administration but without VWF and wherein the titer of inhibitory antibodies is determined with the Bethesda assay.

In another preferred embodiment of the invention such VWF formulated FVIII is administered extravascularly to previously untreated patients, as the generation of inhibitory antibodies against FVIII most likely occurs during the initial doses of FVIII which a so far untreated hemophilia A patient receives.

In yet another preferred embodiment of the invention when administering FVIII together with VWF extravascularly, the administered VWF has a VWF:RCoF/VWF:Ag ratio which is less than 1:0.35, preferentially equal or less than 1:1.05.

Another preferred embodiment of the invention is the use of VWF for the manufacture of a medicament to treat VWD and/or hemophilia A, wherein the administered VWF is administered extravascularly and has a VWF:RCoF/VWF: Ag ratio which is less than 1:0.35 or preferentially less than 1:1.05.

FIGURES

FIG. 1: Pharmacokinetics of 200 U/kg Monoclate-P® injected i.v. or s.c. (n=2/group; mean+SD)

FIG. 2: FVIII activity in plasma of FVIII ko mice following 100 U/kg Monoclate-P® i.v. or s.c. and 1800 U/kg s.c. (mean+SD; n=4-5/timepoint)

FIG. 3: FVIII activity plasma level in FVIII ko mice following 1800 U (FVIII:C)/kg Monoclate-P® or Haemate® P (mean+SD; n=4-5/timepoint)

FIG. 4: Mean FVIII activity+SD up to 2 days following s.c. injection of 900 or 1800 U (FVIII:C)/kg Haemate® P (n=5/timepoint)

FIG. 5: Mean FVIII activity±SD up to 2 days following s.c. injection of 400 U (FVIII:C)/kg Haemate® P, characterized by a varied VWF:Ag/FVIII:C ratio (n=5/timepoint)

FIG. 6: Time course of mean FVIII activity+SD up to 2 days following s.c. injection of 200 U (FVIII:C)/kg Haemate® P, characterized by a typical and increased VWF:Ag/ FVIII:C ratio (n=5/timepoint)

FIG. 7: AUDC (FVIII) increase by increased VWF:Ag/ FVIII:C ratio

FIG. 8: Clot formation time (in TEM) following sc injection of Haemate® P (n=7-24; mean+SD)

FIG. 9: Alpha (in TEM) following sc injection of Haemate® P (n=7-24; mean+SD)

FIG. 10: Comparison of human FVIII:Ag pharmacokinetics in FVIII ko mice following i.v. injection of 100 U (FVIII: C)/kg Haemate® P or Helixate (mean+SD; n=3-5/timepoint)

FIG. 11: Comparison of human FVIII:Ag pharmacokinetics in VWF ko mice following iv injection of 50 U (FVIII:C)/ kg Haemate® P and Monoclate P (mean+SD; n=5-6/timepoint)

FIG. 12: Comparison of FVIII activity in plasma following sc injection of 400 U (FVIII:C)/kg Haemate® P to FVIII ko and VWF ko mice (mean+SD, n=4-5/timepoint FIG. 13: Time course of VWF:Ag following s.c. injection of 2300 U (VWF:Ag)/kg Haemate® P to rabbits (Mean+SD, n=4/timepoint)

FIG. 14: Time course of mean VWF:Ag, VWF:RCo and FVIII:C plasma level+SD up to 3 days following s.c. injection of 523 U(VWF:Ag)/kg (n=5/timepoint)

FIG. 15: Role of VWF for the generation of anti-FVIII antibodies and FVIII-inhibiting antibodies (Bethesda-assay) following i.v. or s.c. administration of FVII FIG. 16: Time course of mean FVIII activity plasma levels±SD following s.c. injection of 500 U (FVIII:C)/kg Haemate® P preparations, characterized by different VWF: RCo/VWF:Ag ratios (n=4/timepoint)

EXAMPLES

Example 1

Assessment of Bioavailability of s.c. Applied Monoclate-P® in Rabbits

200 U/kg of FVIII (Monoclate-P®) was administered via the intravenous (ear vein) route at t=0 or via the subcutaneous (neck) route at t=0 by a single injection to CHB rabbits, weighing about 2.5-3 kg. Blood samples were drawn via the ear vein (contralateral in the case of i.v. injection) for the determination FVIII:Antigen prior to dosing (baseline) and at 5, 15, 30, 45 min., 1, 2, 4, 6, 8 and 24 h (Table 1). The blood was anticoagulated as 10% citrate blood. Human FVIII:Ag was quantified in plasma, processed from blood by centrifugation using a commercial ELISA; Cedarlane Laboratories Ltd. The plasma was stored at −20° C. prior to analysis. FIG. 1 illustrates the poor bioavailability of subcutaneously applied high purity, plasmatic FVIII. Only a minute amount of the s.c. injected FVIII reached the bloodstream. Peak plasma levels reached approximately 0.05 U/mL, which is close to the baseline level of 0.03 U/ml, corresponding to the crossreactivity of the ELISA to rabbit proteins. Baseline corrected, the relative AUDC (bioavailability) of Monoclate-P® was low, i.e. <5%.

AUDC is the area under the plasma concentration-time data curve (calculated according to the trapezoidal rule) and bioavailability is calculated as (AUDC (s.c.)×Dose (i.v.))/ (AUDC (i.v.)×Dose (s.c.))

TABLE 1

Treatment groups (rabbits) for assessment of bioavailability of s.c. applied Monoclate-P ®

| No. | Treatment | Dose (FVIII:C)/volume/ schedule/route | FVIII Concentration | N (m/f) |
|---|---|---|---|---|
| 1 | Monoclate-P ® | 200 U/kg/2.2 mL/kg/i.v. | 91 U/mL | 1 m/ 1 f |
| 2 | Monoclate-P ® | 200 U/kg/2.2 mL/kg/s.c. | 91 U/mL | 1 m/ 1 f |

Example 2

Assessment of Bioavailability of s.c. Applied Monoclate-P® in a Hemophilia A Model (FVIII ko Mice)

Healthy rabbits used as a model to assess the relative bioavailability of Monoclate-P® in example 1 have a physiological, normal level of endogenous FVIII. This circumstance might inhibit the resorption of Monoclate-P® following s.c. injection, resulting in underestimating its relative bioavailability. In addition, an antigen-based approach was required in the rabbit model for a specific quantification allowing a differentiation between the endogenous and the exogenously applied human FVIII. An antigen-based method does however not allow conclusions on the functional activity of the FVIII resorbed.

To address these issues, FVIII knockout (ko) mice weighing about 25 g were used as a Hemophilia A model. These mice do not express FVIII (Bi L. et al, Nature genetics, 1995, Vol 10(1), 119-121; Bi L. et al, Blood, 1996, Vol 88(9), 3446-3450). This allows the quantification of experimentally administered FVIII activity in the plasma of the FVIII ko mice. 100 U/kg or 1800 U/kg of FVIII (Monoclate-P®) was administered via the intravenous (tail vein) route at t=0 by a single injection. With the same design, 100 U/kg of FVIII (Monoclate-P®) was administered via the subcutaneous (neck) route. Under short term anesthesia, blood samples were drawn retroorbitally, anticoagulated using calcium citrate to 10 to 20% citrate blood, processed to plasma and stored at −20° C. for the determination of FVIII activity. For the i.v. injection, sampling timepoints were: At baseline, 5, 30 min, 2, 4, 6 and 24 h, for s.c. injections, an additional sample was taken at t=8 h (Table 2). Quantification of FVIII activity in plasma was performed by a standard, aPTT based approach (Behring Coagulation Timer).

Taken together the result from FVIII ko mice were in line with the results obtained from rabbits. The $AUDC_{0-1d}$ for 100 U (FVIII:C)/kg Monoclate-P® i.v. was about 27.8 h·U/mL, for the same dose applied s.c. 1.5 h·U/mL, corresponding to a bioavailability of about 5%. Increasing the s.c. administered dose almost 20× fold to 1800 U/kg resulted in a rise of $AUDC_{0-1d}$ by only a factor of about 2.5-fold (FIG. 2).

TABLE 2

Treatment groups (FVIII ko mice) for assessment of bioavailability of s.c. applied Monoclate-P ®

| No. | Treatment | Dose (FVIII:C)/volume/ schedule/route | FVIII Concentration | N (total) |
|---|---|---|---|---|
| 1 | Monoclate-P ® | 100 U/kg/0.2 mL/ 20 g/i.v. | 10 U/mL | 35 |

TABLE 2-continued

Treatment groups (FVIII ko mice) for assessment of bioavailability of s.c. applied Monoclate-P ®

| No. | Treatment | Dose (FVIII:C)/volume/ schedule/route | FVIII Concentration | N (total) |
|---|---|---|---|---|
| 2 | Monoclate-P ® | 100 U/kg/0.2 mL/ 20 g/s.c. | 10 U/mL | 30 |
| 3 | Monoclate-P ® | 1800 U/kg/0.4 mL/ kg/s.c. | 90 U/mL | 40 |

Example 3

Assessment of Bioavailability of s.c. Administered Haemate® P in a Hemophilia A Model (FVIII ko Mice)

Surprisingly, when the same dose of FVIII was administered s.c. to FVIII ko mice using a VWF containing product (Haemate® P) a clear rise of FVIII activity in plasma was observed (FIG. 3). Using the same study design and methods as in example 2, the $AUDC_{0-2d}$ was strikingly about 2 higher with Haemate® P as compared to the same dose of Monoclate-P® (Table 3): The peak plasma concentration achieved by Haemate® P was about 2.5 to 3 fold higher, with a maximal difference of up to 10 fold. From this difference, a firm conclusion on the beneficial role of VWF for the resorption of FVIII from the subcutaneous space can be drawn. To further explore the role of VWF the Haemate® P dose was reduced by 50% to 900 U (FVIII:C)/kg in a repeat experiment (Table 4; FIG. 4). Surprisingly this led not to a smaller $AUDC_{0-1d}$ (Table 5). Against the background of this result it appears plausible that at such high doses resorption mechanisms might be saturated. Assessing the improvement achievable by a VWF containing solution therefore underestimates the raise of FVIII plasma levels, which can by achieved.

TABLE 3

Comparison of AUDC for FVIII activity plasma level in FVIII ko mice following 1800 U/kg Monoclate-P ® or Haemate ® P

| No. | Treatment | $AUDC_{0-2d}$ [h · U/mL] | VWF:Ag/FVIII:C ratio |
|---|---|---|---|
| 1 | 1800 U (FVIII:C)/kg Haemate ® P | 11.2 | 3:1 |
| 2 | 1800 U (FVIII:C)/kg Monoclate-P ® | 5.6 | |

TABLE 4

Treatment groups (FVIII ko mice) for studying the effect of dose reduction

| No. | Treatment | Dose (FVIII:C)/volume/ schedule/route | FVIII Concentration | N (total) |
|---|---|---|---|---|
| 1 | Haemate ® P | 1800 U/kg/0.56 mL/ 20 g b.w./ single t = 0/s.c. | 64 U/mL | 40 |
| 2 | Haemate ® P | 900 U/kg/0.64 mL/ 20 g b.w./ single t = 0/s.c. | 28 U/mL | 40 |

TABLE 5

Comparison of AUDC for FVIII activity plasma level in FVIII ko mice
following 900 and 1800 U (FVIII:C)/kg Haemate ® P

| No. | Treatment | AUDC$_{0-1d}$ [h · U/mL] | VWF:Ag/FVIII:C ratio |
|---|---|---|---|
| 1 | 1800 U (FVIII:C)/kg Haemate ® P | 9.8 | 3:1 |
| 2 | 900 U (FVIII:C)/kg Haemate ® P | 9.2 | |

Example 4

Assessment of Role of the VWF:Ag/FVIII:C Ratio for Bioavailability of FVIII in Hemophilia A Mice Given the surprising finding of the impact of VWF, the ratio of VWF:Ag over FVIII:C in the solution applied was systematically varied. The ratio of VWF:Ag/FVIII:C in Haemate® P is typically in the range of about 3:1. As a next step a VWF:Ag/FVIII:C ratio of 0.9:1 (Table 6) was tested. The same methods as in example 2 were applied. FIG. 5 illustrates that at a dose level of 400 U (FVIII:C)/kg FVIII:C baseline level was still not reached after about 48 h for Haemate® P (VWF:Ag/FVIII:C ratio of 3:1). For the "low VWF:Ag" solution, FVIII:C level returned to baseline already after about 30 hours. In addition, with the VWF:Ag/FVIII:C ratio of 3:1 the peak FVIII plasma levels were about 2× to 3× fold higher as compared to the ratio of 0.9:1. Decreasing the VWF:Ag/FVIII:C ratio from 3:1 to 0.9:1 reduced the AUDC$_{0-2d}$ to just 22% of the AUDC$_{0-2d}$ achieved at with the formulation at the ratio of 3:1. It can be concluded that at this dose level, increasing the VWF:Ag/FVIII:C ratio raises the AUDC and the peak plasma levels of FVIII and results in a longer period with elevated FVIII levels in plasma. In a further experiment a VWF:Ag/FVIII:C ratio of 6.5:1 (Table 6) was tested at a dose level of 200 U (FVIII:C)/kg. Surprisingly raising the VWF:Ag/FVIII:C ratio from 3:1 to 6.5:1 resulted in a similarly high FVIII:C peak level, however, FVIII:C was observed in plasma for a period about 2× to 3× times longer (FIG. 6). Correspondingly, the AUDC$_{0-1d}$ raised about 2.7 times. Seemingly VWF:Ag can not only affect the in vivo recovery of FVIII:C but can also lead to higher peak levels of FVIII and longer period of elevated FVIII:C levels.

Summarizing and interpolating the results on the FVIII dose-corrected AUDC from the previous examples leads to a clear relationship of VWF:Ag/FVIII:C ratio and the fraction of FVIII reaching circulation (FIG. 7). Over a broad range, the relationship appears to be quite linear. This relationship allows the firm conclusion that also at higher VWF:Ag/FVIII:C ratios, than those tested so far, the fraction of FVIII transported to circulation would further increase. Due to the linear steepness of the relationship, it appears reasonable to hypothesize that for ratios of at least 10:1 and possibly even 20:1, about 2× or 3× fold of the maximal ratio tested so far, a further increase in the AUDC (FVIII:C) after subcutaneous administration can be expected.

TABLE 6

Treatment groups (FVIII ko mice) for assessment of role of VWF:Ag/FVIII:C ratio

| No. | Treatment | Dose/volume/schedule/route | FVIII Concentration | N (total) |
|---|---|---|---|---|
| 1 | Haemate ® P ® typical ratio (3:1) | 400 U (FVIII:C)/kg + 1150 U (VWF:Ag)/kg/kg/0.2 mL/20 g b.w./single t = 0/s.c. | 40 U/mL | 25 |
| 2 | Humate-P ® "low VWF" (0.9:1) | 400 U/kg (FVIII:C)/kg + 370 U (VWF:Ag)/kg/kg/0.2 mL/20 g b.w./t = −0 h./s.c | 40 U/mL | 25 |
| 3 | Haemate ® P ® typical ratio (3:1) | 200 U (FVIII:C)/kg + 570 U (VWF:Ag)/kg/kg/0.2 mL/20 g b.w./single t = 0/s.c. | 20 U/mL | 20 |
| 4 | Humate-P ® "high VWF" (6.5:1) | 200 U/kg (FVIII:C)/kg + 1300 U (VWF:Ag)//kg kg/0.2 mL/20 g b.w./t = −0 h./s.c. | 20 U/mL | 25 |

Example 5

Determination of Minimal Haemate® P Dose (s.c.) Required for Correction of Coagulation of Hemophilia A Mice As a next step the question was addressed which dose of Haemate® P (typical VWF:Ag/FVIII:C ratio of 3:1) would be required to correct the coagulation deficit of FVIII ko mice. For this purpose FVIII ko mice were treated s.c. with Haemate® P and the consequences for coagulation were quantified by means of standard thrombelastography equipment. The in-TEM® assay using whole blood with a Roteg® 05 analyzer was performed. Blood was sampled retroorbitally and analysed immediately upon sampling, using the in-TEM® reagent to start the thrombelastography; the protocol used essentially reflects the guidance for human blood analysis provided by the manufacturer of the equipment (Pentapharm, GmbH, Munich, Germany). In brief, the reaction was started by adding the in-TEM® reagent to the blood samples which were incubated at 37° C. in the ROTEG instrument. Overall the procedure reflects the approach described for hemophilia A mice in K. A. Landskroner et. al., Haemophilia (2005), 11, 346-352. Applying the in-TEM® assay to FVIII deficient blood, typically the clotting time, CT, and clot formation time, CFT, are prolonged, the alpha-angle (and correspondingly the maximal velocity, maxVel) is decreased, the time to observation of the maximal velocity, t-MaxVel, is increased; minimal if at all any changes are observed in the integrated area under the coagulation curve (AUC) and the maximal clot firmness, MCF remains normal.

Subcutaneous injection of 100, 50 or 25 U (FVIII:C)/kg Haemate® P resulted in a dose dependent reversal of the alpha angle and the clot formation time (CFT) of FVIII ko mice (Tab. 7-10; FIGS. 8 and 9). Table 11 details the results achieved with an intravenous infusion of 25 U (FVIII:C)/kg Haemate® P. The degree of correction corresponds to about the subcutaneous injection of an intravenous infusion of 100 U (FVIII:C)/kg Haemate® P, i.e. the subcutaneous treatment with the VWF containing formulation of FVIII required just an about 4 times higher dose than the intravenous infusion in order to achieve a comparable level of hemostasis correction.

Using Haemate® P, a dose as low as 50 U (FVIII:C)/kg was sufficient for a complete correction of the coagulation defect for about one day. The correction of hemostasis lasted even longer with higher doses being applied; i.e. the correction achieved by 100 U (FVIII:C)/kg lasted for about 2 days. In order to project on this basis the dose required for substantially improving coagulation in hemophilia A patients, it has to be taken into account that healthy mice have an endogenous FVIII level about 2× to 3× higher as compared to healthy humans. Thus the dose of 50 U (FVIII:C)/kg translates into an equivalent of about 15-25 U (FVIII:C)/kg in humans. This corresponds to a dose of FVIII a Hemophilia A patient on prophylactic treatment receives via i.v. administration by conventional treatment. This would also correspond to an injection volume, well suitable for s.c. injections, even for adult patients. In addition, this perspective illustrates the pronounced correction of hemostasis achieved by s.c. injection of a full length FVIII based on a formulation with VWF. This also points to the conclusion that the FVIII plasma level reached in patients may at least suffice for a prophylactic treatment—a situation for which the convenience of a non-intravenous injection would play a major role for the quality of life for the patients.

TABLE 7

Treatment groups or thrombelastography assessment

| No. | Treatment | Dose (FVIII:C)/volume/schedule/route | FVIII Concentration | N (m/f) |
|---|---|---|---|---|
| 1 | No treatment | na | na | 19 (12/7) |
| 2 | Haemate ® P | 100 U/kg/0.2 mL/20 g b.w./t = 0 h/s.c. | 10 U/mL | 56 (37/19) |
| 3 | Haemate ® P | 50 U/kg/0.2 mL/20 g b.w./t = 0 h/s.c. | 5 U/mL | 24 (20/4) |
| 4 | Haemate ® P | 25 U/kg/0.2 mL/20 g b.w./t = 0 h/s.c. | 2.5 U/mL | 48 (25/23) |
| 5 | Haemate ® P | 25 U/kg/0.2 mL/20 g b.w./t = 0 h/i.v. | 2.5 U/mL | 25 (25/0) |

TABLE 8 in-TEM ® results following subcutaneous administration of 100 U (FVIII:C)/kg Haemate ® P

| No. | Time-point [h] | CT [sec] | CFT [sec] | Alpha-Angle [°] | Max Vel | t-MaxVel [sec] | AUC | MCF [mm] | N |
|---|---|---|---|---|---|---|---|---|---|
| 1 | 0 | 199 ± 68 | 68 ± 27 | 76 ± 5 | 22 ± 8 | 250 ± 89 | 7184 ± 609 | 72 ± 6 | 19 |
| 2 | 5 | 190 ± 57 | 45 ± 15 | 82 ± 3 | 37 ± 9 | 232 ± 69 | 7541 ± 519 | 76 ± 5 | 9 |
| 3 | 8 | 177 ± 36 | 38 ± 6 | 82 ± 1 | 36 ± 4 | 205 ± 41 | 7037 ± 152 | 71 ± 2 | 12 |
| 4 | 16 | 240 ± 60 | 58 ± 11 | 79 ± 2 | 26 ± 3 | 289 ± 67 | 7306 ± 306 | 72 ± 3 | 8 |
| 5 | 20 | 199 ± 48 | 58 ± 13 | 78 ± 2 | 26 ± 5 | 241 ± 58 | 6795 ± 295 | 68 ± 3 | 7 |
| 6 | 24 | 207 ± 50 | 54 ± 14 | 79 ± 3 | 27 ± 7 | 242 ± 57 | 6933 ± 314 | 69 ± 3 | 8 |
| 7 | 32 | 189 ± 25 | 50 ± 5 | 81 ± 1 | 29 ± 3 | 238 ± 34 | 7548 ± 161 | 76 ± 2 | 4 |
| 8 | 48 | 230 ± 99 | 70 ± 27 | 76 ± 5 | 22 ± 8 | 293 ± 38 | 7161 ± 278 | 72 ± 3 | 8 |

TABLE 9 in-TEM ® results following subcutaneous administration of 50 U (FVIII:C)/kg Haemate ® P

| No. | Time-point [h] | CT [sec] | CFT [sec] | Alpha-Angle [°] | MaxVel | t-MaxVel [sec] | AUC | MCF [mm] | N |
|---|---|---|---|---|---|---|---|---|---|
| 1 | 0 | 199 ± 68 | 68 ± 27 | 76 ± 5 | 22 ± 8 | 250 ± 89 | 7184 ± 609 | 72 ± 6 | 19 |
| 2 | 5 | 167 ± 71 | 46 ± 13 | 81 ± 2 | 31 ± 6 | 206 ± 88 | 7211 ± 398 | 72 ± 4 | 8 |
| 3 | 8 | 211 ± 43 | 51 ± 13 | 80 ± 3 | 32 ± 12 | 258 ± 54 | 7281 ± 567 | 73 ± 6 | 8 |
| 4 | 16 | 225 ± 89 | 66 ± 24 | 77 ± 5 | 22 ± 8 | 283 ± 113 | 7102 ± 305 | 71 ± 3 | 8 |
| 5 | 20 | 172 ± 35 | 49 ± 12 | 80 ± 2 | 28 ± 6 | 214 ± 54 | 7083 ± 337 | 71 ± 3 | 8 |

TABLE 10 in-TEM ® results following subcutaneous administration of 25 U (FVIII:C)/kg Haemate ® P

| No. | Time-point [h] | CT [sec] | CFT [sec] | Alpha-Angle [°] | MaxVel | t-MaxVel [sec] | AUC | MCF [mm] | N |
|---|---|---|---|---|---|---|---|---|---|
| 1 | 0  | 199 ± 68 | 68 ± 27 | 76 ± 5 | 22 ± 8 | 250 ± 89  | 7184 ± 609 | 72 ± 6 | 19 |
| 2 | 5  | 223 ± 54 | 60 ± 14 | 78 ± 3 | 23 ± 5 | 271 ± 71  | 7072 ± 200 | 71 ± 2 | 16 |
| 3 | 8  | 181 ± 66 | 53 ± 22 | 79 ± 4 | 28 ± 9 | 224 ± 90  | 7143 ± 335 | 72 ± 3 | 24 |
| 4 | 16 | 248 ± 83 | 75 ± 28 | 75 ± 5 | 21 ± 9 | 313 ± 110 | 7304 ± 598 | 73 ± 6 | 12 |
| 5 | 20 | 191 ± 47 | 66 ± 15 | 77 ± 3 | 20 ± 5 | 231 ± 57  | 7009 ± 343 | 70 ± 3 | 8  |

TABLE 11 in-TEM ® results following intravenous administration of 25 U (FVIII:C)/kg Haemate ® P

| No. | Time-point [h] | CT [sec] | CFT [sec] | Alpha-Angle [°] | MaxVel | t-MaxVel [sec] | AUC | MCF [mm] | N |
|---|---|---|---|---|---|---|---|---|---|
| 1 | 0  | 199 ± 68 | 68 ± 27 | 76 ± 5 | 22 ± 8 | 250 ± 89 | 7184 ± 609 | 72 ± 6 | 19 |
| 2 | 4  | 158 ± 24 | 36 ± 4  | 83 ± 1 | 39 ± 5 | 184 ± 24 | 7206 ± 150 | 73 ± 1 | 4 |
| 3 | 8  | 192 ± 15 | 40 ± 4  | 80 ± 1 | 35 ± 3 | 222 ± 16 | 7300 ± 119 | 74 ± 1 | 4 |
| 4 | 16 | 196 ± 14 | 40 ± 3  | 82 ± 1 | 35 ± 3 | 228 ± 14 | 7059 ± 118 | 71 ± 1 | 4 |
| 5 | 24 | 192 ± 75 | 47 ± 5  | 80 ± 1 | 29 ± 3 | 228 ± 81 | 6778 ± 410 | 68 ± 4 | 4 |
| 6 | 32 | 181 ± 19 | 37 ± 3  | 83 ± 1 | 42 ± 4 | 215 ± 20 | 7465 ± 170 | 75 ± 2 | 4 |

Example 6

Exclusion of Intra-Vascular Compartment as Location of Beneficial Effects of VWF:Ag for Increasing Bioavailability Upon s.c. Injections VWF is a multifunctional protein. In addition to its direct role in hemostasis, vWF also plays an important role in stabilizing and protecting FVIII in circulation. Patients suffering from a VWF disease type III a disorder in which VWF:Ag is virtually undetectable, clearly demonstrate this, as they also suffer from a secondary deficiency of FVIII. Against this background one may hypothesize that in von Willebrand disease patients, the bioavailability of non-VWF formulated FVIII may actually not differ from VWF formulated FVIII. In the first case, FVIII would just get rapidly cleared from circulation, while it is stabilized in circulation by VWF in the second.

In order to test this hypothesis, FVIII ko were injected with a single treatment at t=0, i.v. (tail vein) with 100 U(FVIII:C)/kg, kg Helixate or Haemate® P. In addition VWF ko mice were injected by a single treatment at t=0, i.v. (tail vein) with 50 U(FVIII:C)/kg Helixate or Haemate® P. These VWF ko mice lack exons 4 and 5 and do not express endogenous VWF (Denis C. et al, Proc. Natl. Acad. Sci. USA, 1998, Vol 95, 9524-9529). Blood samples were retroorbitally drawn under short term anaesthesia, further sample processing was performed as in example 2. All samples were quantified on their human FVIII:Ag concentration using a commercial ELISA (Cedarlane Laboratories Ltd.).

FIG. 10 illustrates the almost identical pharmacokinetics of a high purity FVIII and a VWF formulated FVIII product following i.v. injection in FVIII ko mice. This shows that human FVIII requires no human VWF in mice for stabilization in circulation. There is, however, a substantial difference if there is no endogenous VWF present to stabilize human FVIII in circulation (FIG. 11): In mice having no endogenous VWF in circulation (VWF ko mice) the recovery of a high purity FVIII product (Monoclate-P®) is lower as compared to a VWF formulated product (Haemate® P) and it gets cleared more rapidly as well.

Taken together with the results from FVIII ko mice (FIG. 10), this also demonstrates that human FVIII gets equally stabilized by the animals' heterologous VWF as compared to human VWF. Since obviously additional human VWF:Ag in circulation does not further stabilize human FVIII:C following i.v. application to FVIII ko mice, the stabilization of FVIII:C by VWF:Ag containing formulation following s.c. application must be mediated at a compartment different than the vascular system. Integrating these findings one can conclude that the improved bioavailability observed following s.c. injection of a VWF:Ag formulated FVIII as long as sufficient VWF:Ag is present in the circulation is not the consequence of stabilizing FVIII:C in circulation, but along the processes involved in reaching the circulation. These processes might encompass the protection of FVIII from proteases, degrading the protein prior to reaching circulation. The increased bioavailability might also represent the consequence of, potentially active, transport mechanisms. They may work more efficiently on VWF, which then passively co-transports FVIII, or they might more efficiently work on a VWF-FVIII complex than on FVIII alone.

TABLE 12

Treatment groups for comparison of pharmacokinetics of high purity FVIII to VWF:Ag formulated FVIII in FVIII ko and VWF ko mice

| No. | Species | Treatment | Dose (FVIII:C)/volume/schedule/route | N |
|---|---|---|---|---|
| 1 | FVIII ko mouse | Helixate | 100 U/kg/0.2 mL/20 g b.w./ t = 0 h/i.v. | 6 |
| 2 | FVIII ko mouse | Haemate ® P | 100 U/kg/0.2 mL/20 g b.w./ t = 0 h/i.v. | 6 |

TABLE 12-continued

Treatment groups for comparison of pharmacokinetics of high purity
FVIII to VWF:Ag formulated FVIII in FVIII ko and VWF ko mice

| No. | Species | Treatment | Dose (FVIII:C)/volume/ schedule/route | N |
|---|---|---|---|---|
| 3 | VWF ko mouse | Monoclate-P ® | 50 U/kg/0.2 mL/20 g b.w./ t = 0 h/i.v. | 20 |
| 4 | VWF ko mouse | Haemate ® P | 50 U/kg/0.2 mL/20 g b.w./ t = 0 h/i.v.. | 20 |

Example 7

Therapy of von Willebrand Disease Related FVIII Deficiency by s.c. Injections—Benefit of a VWF:Ag Formulated FVIII Solution Decreased FVIII:C levels are not only causal for the bleeding phenotype in hemophilia A, but play also a crucial role in von Willebrand disease (VWD). As detailed in Example 7, decreased FVIII:C levels result from the disturbed stabilization by VWF. As VWF:Ag formulated FVIII was demonstrated suitable for s.c. applications of hemophilia A, it was tested whether FVIII:C levels might also be increased in VWD (Table 13). 400 U (FVIII:C)/kg Haemate® P was injected s.c. to VWF ko and FVIII ko mice and their plasma was analysed on FVIII:C activity. The same study design and methods as in example 2. As compared to healthy control mice with an endogenous FVIII:C level of about 3 U/mL, a reduced FVIII:C baseline level is common both VWF ko and FVIII ko mice, while VWF ko mice additionally lack their endogenous VWF. Therefore, the beneficial role of s.c. applied VWF:Ag might be most pronounced in these mice, as the processes involved in FVIII reaching circulation, might be fully available to the s.c. applied VWF:Ag. FIG. 12 shows that in fact, the FVIII:C raise is much more pronounced in VWF ko mice as compared to FVIII ko mice. Baseline adjusted, the peak levels were up to 6 fold higher and the AUDC was at least 3 fold higher in VWF ko mice. This indicates that in VWD, patients might also profit from a s.c. therapy with a VWF:Ag formulated FVIII product, potentially even more than hemophilia A patients, as VWF:Ag has a twofold effect: a) stabilization/enhancement of uptake of s.c. applied FVIII and b) subsequent stabilization of the FVIII once it has reached plasma.

TABLE 13

Treatment groups for comparison of pharmacokinetics of VWF:Ag
formulated FVIII in FVIII ko and VWF ko mice

| No. | Species | Treatment | Dose (FVIII:C)/volume/ schedule/route | N |
|---|---|---|---|---|
| 1 | FVIII ko mouse | Haemate ® P | 400 U/kg/0.2 mL/20 g b.w./ t = 0 h s.c. | 25 |
| 2 | VWF ko mouse | Haemate ® P | 400 U/kg/0.2 mL/20 g b.w./ t = 0 h s.c. | 25 |

Example 8

Therapy of VWF Deficiency in von Willebrand Disease Following s.c. Injections of VWF:Ag Example 8 summarizes data showing the potential therapy of FVIII deficiency in VWD by s.c. injections. In order to test whether also the VWF deficiency can be treated by s.c. injection of a VWF product, CHB rabbits were injected with 2300 U/kg VWF:Ag (Haemate® P) via the subcutaneous route at t=0 by a single injection. The rabbits were weighing about 2.5-3 kg. Blood samples were drawn via the ear vein for the determination human VWF:Ag prior to dosing (baseline) and at 1, 2, 4, 6, 24, 30 h, 2 and 3 days following treatment (Table 14). The blood was anticoagulated as 10% citrate blood. Human VWF:Ag was quantified in plasma, processed from blood by centrifugation using a commercial ELISA; Roche Diagnostics. The plasma was stored at −20° C. prior to analysis. It was surprisingly found that also VWF though even larger than FVIII enters the circulation, which offers an option for a therapy of von Willebrand Disease also based on s.c. administration of VWF:Ag (FIG. 13).

TABLE 14

Treatment group for assessment of resorption of VWF:Ag following
s.c. injection to rabbits

| No. | Treatment | Dose/volume/schedule/route | N |
|---|---|---|---|
| 1 | Haemate ® P | 2300 U/kg VWF:Ag/12.6 mL/kg b.w./t = 0 h s.c. | 4 |

Plasma samples of were analyzed for human VWF:Ag using a commercially available ELISA kit (VWF:Ag, Roche Diagnostics). It was surprisingly found that also VWF though even larger than FVIII enters the circulation, which offers an option for a therapy of von Willebrand Disease also based on s.c. administration of VWF:Ag.

Example 9

S.C. Administration of VWF:Ag without FVIII in VWD Ko Mice

High purity VWF was injected subcutaneously to VWF ko mice at a dose of 523 U(VWF:Ag)/kg (Table 15). Blood samples were drawn retroorbitally for the determination human VWF:Ag prior to dosing (baseline) and pre-dose, and at 2, 4, 6, 16 hours, 1, 2 and 3 days following treatment. The blood was anticoagulated as 10% citrate blood. Human VWF: Ag was quantified in plasma, processed from blood by centrifugation using a commercial ELISA; Roche Diagnostics. The plasma was stored at −20° C. prior to analysis. VWF:Ag plasma level raised following this treatment to peak levels of about 0.1-0.2 U(VWF:Ag)/mL (FIG. 14). The timecourse of VWF:RCo appeared somewhat steeper, reflecting a combination of transport to plasma and clearance from there. In addition to the assessment of human VWF being transport to plasma in this VWD model, it was analyzed at the same time points, whether this raise of plasmatic (human) VWF level results in a secondary raise of endogenous FVIII:C levels in plasma, due to the restored stabilization of endogenous FVIII: C. Indeed, a raise of FVIII:C in plasma was observed, which occurred somewhat delayed as compared to the timecourse of VWF. This points to the conclusion that s.c. applied VWF is not only transported to plasma, but additionally retains functional activity, as shown by the VWF:RCo level, as well as its function to stabilize endogenous FVIII:C. The raise of FVIII was, however not as pronounced as observed in example 7, thus the raise of FVIII:C following s.c. injection of a VWF formulated FVIII solution represents both transport of FVIII from the subcutaneous space as well as stabilization of endogenous FVIII.

TABLE 15

Treatment groups for s.c. application of pure VWF to VWF ko mice

| No. | Treatment | Dose/volume/schedule/route | N |
|---|---|---|---|
| 1 | Human Von Willebrand Factor | 523 U (VWF:Ag)/kg/0.2 mL/20 g b.w./single at t = 0/subcutaneous | 40 |

Example 10

Assessment of Immunogenicity of VWF Formulated FVIII in a Hemophilia A Model (FVIII ko Mice)

The frequent development of neutralizing antibodies against FVIII is a major problem for the treatment of patients with severe hemophilia A. About 25% of these patients develop these inhibitory antibodies, neutralizing the activity of FVIII. Accordingly FVIII substitution does not help any more to correct the patients' hemostasis. While such inhibitory antibodies typically are generated by the first couple of treatments, e.g. in previously untreated patients (PUPs), it is currently very difficult to predict which patients will suffer from this complication. Whether the particular FVIII concentrate used plays a role in this is a topic of controversial discussion in the scientific literature. From other proteins, designed to achieve a maximal immune response it is at least clear, that the application mode plays a crucial role, i.e. i.v. injections are typically less immunogenic than s.c. injections.

This example addressed the question, whether the increased FVIII bioavailability by a VWF formulation may be paralleled by an increased immunogenicity of FVIII, in an animal model representing severe hemophilia A patients. FVIII ko mice were treated as detailed in Table 16.

The total anti-FVIII titer was determined using ELISA plates coated with Helixate®. In brief, the first immunological reaction was the binding of antibodies in the plasma sample against human FVIII coated onto the microtitration wells. Following a washing step, these captured antibodies are detected with a peroxidase labeled anti mouse IgG, i.e. a second immune reaction. The activity of peroxidase is determined photometrically after adding tetramethylbenzidine and stopping the reaction after a predetermined time period with sulphuric acid 0.5 N.

The Bethesda-assay was performed according to the following procedure. In brief, 1 BU is defined as the reciprocal of the dilution of test plasma that inhibits 50% of total FVIII activity after a 2 hour incubation at 37° C. Plasma sample dilutions and healthy human control plasma were mixed and incubated at 37° C. for 2 hours. Residual FVIII activity was quantified post-incubation. Accordingly the data were reported as Bethesda Units (BU) and normalized to the highest total anti-FVIII titer observed, to allow a direct comparison.

The data summarized in table 17 indicate that following an i.v. injection, the VWF formulated FVIII (Haemate® P) generated a slightly lower anti-FVIII titer than the VWF free FVIII product (Helixate®). Such an observation is in line with a trend in the scientific literature, pointing to a potentially lower risk for generating inhibitory antibodies by VWF formulated products (Goudemand J., Haemophilia, Vol. 13 Suppl. 5: 47-51, 2007; Ettingshausen C. E., Kreuz W., Haemophilia, Vol. 12 Suppl. 6: 102-106, 2006). There was essentially no difference whether the comparison was based on all anti FVIII antibodies or more specifically on those inhibiting FVIII activity.

In the groups treated s.c. with either the VWF formulated or VWF free FVIII in combination with complete Freud's adjuvant (cFA) and at a slightly different schedule, the immune response was higher than in the i.v. groups, as expected. More importantly, however, it was found surprisingly when FVIII was formulated with VWF for the s.c. injection the immune response was much lower than for the s.c. injection of FVIII which was not formulated with VWF.

This was the case for both the total anti-FVIII titer as well as for the inhibitors. In order to exclude that this surprising observation is due to an interference with the immunostimulating effect of the adjuvant as well as the treatment schedule, the experiment was repeated without adjuvant with the identical treatment schedule as for the i.v. comparison. In line with finding from the combination with adjuvant a higher titer following s.c. injection of Helixate® (FIG. 1) was observed as compared to the i.v. injection of Helixate®. The results confirmed that also in a slightly different design, a VWF formulation decreases the immune response to FVIII following s.c. injection. as compared to FVIII which was not formulated with VWF. This was assessed at two dose levels. The dose of 100 U(FVIII:C)/kg of Haemate® P was chosen to achieve a FVIII level in plasma, which is similar to the plasma level achieved by 200 U(FVIII:C)/kg of Helixate®, following their s.c. application. The 200 U(FVIII:C)/kg dose of Haemate®P was chosen to apply the same FVIII dose as with Helixate®, locally, in order to achieve similar FVIII levels at both compartments, likely to be critical for the level of immune response observed, i.e. either in circulation with the low dose or in the subcutaneous space with the high dose. Independent of the dose as well as the approach to quantify the immune response, the reaction to VWF formulated FVIII (Haemate P®) was much less pronounced as compared to Helixate®. As the specific FVIII activity of Helixate® is substantially higher as compared to Haemate® P, while the immune response should be directed to inactive FVIII as well, the beneficial effect of VWF is likely underestimated in this example.

Taken together these data demonstrate that surprisingly there was a large benefit of the VWF formulation for achieving a minimized formation of anti-FVIII antibodies and specifically inhibiting anti-FVIII antibodies upon s.c. administration, which was substantially larger than following the i.v. administration. This was even more surprising against the background, that the plasma level in the high dose s.c. group of Haemate®P was higher that the plasma levels achieved by the s.c. application of Helixate®, due to the higher bioavailability by the VWF formulation.

TABLE 16

Treatment groups (FVIII ko mice) for assessment of the role of VWF on the immunogenicity of s.c. applied FVIII

| No. | Treatment | Dose (FVIII:C)/volume/schedule/route | N |
|---|---|---|---|
| 1 | Helixate ® | 100 U/kg/0.2 mL/20 g b.w./ t = d 0, 4, 7, 11 i.v. | 10 |
| 2 | Haemate ® P | 100 U/kg/0.2 mL/20 g b.w./ t = d 0, 4, 7, 11 i.v.. | 10 |
| 3 | Helixate ® | 100 U/kg/0.2 mL/20 g b.w./ t = d 0, 14, 25 s.c (+ cFA d 0) | 5 |
| 4 | Haemate ® P | 100 U/kg/0.2 mL/20 g b.w./ t = d 0, 14, 25 s.c (+ cFA d 0) | 5 |
| 5 | Helixate ® | 200 U/kg/0.2 mL/20 g b.w./ t = d 0, 4, 7, 11 s.c | 5 |
| 6 | Haemate ® P | 100 U/kg/0.2 mL/20 g b.w./ t = d 0, 4, 7, 11 s.c | 8 |
| 7 | Haemate ® P | 200 U/kg/0.2 mL/20 g b.w./ t = d 0, 4, 7, 11 s.c | 9 |

TABLE 17

Role of VWF for the titer of anti-FVIII antibodies and FVIII-inhibiting antibodies following treatment i.v. or s.c. application of FVIII

| No. | Treatment | Dose (FVIII:C)/volume/ schedule/route | Total anti-FVIII titer | Bethesda-assay[1] [BU/mL] |
|---|---|---|---|---|
| 1 | Helixate ® | 100 U/kg/0.2 mL/20 g b.w./ t = d 0, 4, 7, 11 i.v.. | 571 | 854 |
| 2 | Haemate ® P | 100 U/kg/0.2 mL/20 g b.w./ t = d 0, 4, 7, 11 i.v. | 268 | 737 |
| 3 | Helixate ® | 100 U/kg/0.2 mL/20 g b.w./ t = d 0, 14, 25 s.c (+ cFA d 0) | 16648 | 16648 |
| 4 | Haemate ® P | 100 U/kg/0.2 mL/20 g b.w./ t = d 0, 14, 25 s.c (+ cFA d 0) | 739 | 619 |
| 5 | Helixate ® | 200 U/kg/0.2 mL/20 g b.w./ t = d 0, 4, 7, 11 s.c | 2417 | 4479 |
| 6 | Haemate ® P | 100 U/kg/0.2 mL/20 g b.w./ t = d 0, 4, 7, 11 s.c | 365 | 501 |
| 7 | Haemate ® P | 200 U/kg/0.2 mL/20 g b.w./ t = d 0, 4, 7, 11 s.c | 489 | 1031 |

[1] data normalized to the highest anti-FVIII titer observed (group 3)

Example 11

Role of the VWF:Ag/VWF:RCo Ratio on Bioavailability of VWF and FVIII:C (Formulated with VWF) Following s.c. Application The previous examples have shown that s.c. applied VWF surprisingly reaches circulation. In addition it was demonstrated that a formulation of FVIII with VWF increases the bioavailability of FVIII:C in FVIII ko mice, following s.c. application. This example examines the potential role of the VWF multimer pattern in this respect. To address this topic two groups of FVIII ko mice were treated s.c. with the same FVIII:C dose (500. U/kg) and essentially the same VWF:Ag dose (500 or 520 U/kg). Their VWF:RCo dose differed, however, by a factor of about three fold. This was achieved by using VWF solutions, which were characterized by a differential VWF multimer pattern, i.e. either consisting of either predominantly small or large multimers. The VWF:RCo/VWF:Ag ratio varied accordingly from 1:1.05 to 1:0.35 (Table 18). An additional group with untreated FVIII ko mice was included as reference. Schedule, route and injection volume was identical for all groups, i.e. administration was performed subcutaneously at t=0 with an injection volume of 0.2 mL/20 g b.w.

TABLE 18

Treatment groups (FVIII ko mice) for assessment of role of VWF:RCo/VWF:Ag ratio

| | | Dose | | | | | |
|---|---|---|---|---|---|---|---|
| No. | Treatment | FVIII:C [U/kg] | VWF:Ag [U/kg] | VWF:RCo [U/kg] | VWF:Ag/ FVIII:C ratio | VWF:RCo/ VWF:Ag ratio | N |
| 1 | No treatment | Not appl. | Not appl. | Not appl. | Not appl. | Not appl. | 5 |
| 2 | "VWF-monomer" Haemate ® P | 500 | 500 | 474 | 1:1 | 1:1.05 | 20 |
| 3 | "VWF-multimer" Haemate ® P | 500 | 520 | 1494 | 1.04:1 | 1:0.35 | 20 |

Although groups 2 and 3 were treated with the same FVIII:C dose and essentially the same VWF:Ag dose, a substantial difference in the FVIII:C concentration in plasma was observed (FIG. 16). Although there was no relevant difference in the VWF:Ag dose, the FVIII:C plasma level increase above baseline was surprisingly about two fold higher in the group treated with the "monomer" preparation of Haemate® P as compared to the group treated with the "multimer" preparation. In line with this, the FVIII raise observed with the "monomer" preparation appeared to result in a higher FVIII:C plasma level than achieved with Haemate® P at a comparable dose (FIG. 5). It is concluded that in contrast to the role in hemostasis, a VWF preparation containing many multimers, i.e. with VWF:RCo/VWF:Ag ratio of at about 1:0.35, results in a decreased FVIII bioavailability when administered s.c. as compared to the higher and longer lasting FVIII increase achieved by a VWF preparation containing many monomers.

The invention claimed is:

1. A method for treating von Willebrand disease (VWD) and/or hemophilia A, comprising extravascularly administering a composition comprising purified von Willebrand factor (VWF) and factor VIII (FVIII), wherein the ratio of VWF antigen (VWF:Ag) to factor VIII-coagulant (FVIII:C) is larger than 5:1, wherein the VWF has a ratio of von Willebrand factor to ristocetin cofactor activity (VWF:RCoF) to von Willebrand factor antigen (VWF:Ag) which is equal to or less than 1:1.05, wherein the VWF is not chemically modified.

2. A method for treating von Willebrand disease (VWD) and/or hemophilia A, comprising extravascularly co-administering von Willebrand factor (VWF) and factor VIII (FVIII), wherein the ratio of VWF antigen (VWF:Ag) to factor VIII-coagulant (FVIII:C) is larger than 5:1, wherein the VWF has a ratio of von Willebrand factor to ristocetin cofactor activity (VWF:RCoF) to von Willebrand factor antigen (VWF:Ag) which is equal to or less than 1:1.05, wherein the VWF is not chemically modified, and wherein the extravascular co-administration:
   a) prolongs the time period during which the FVIII activity in plasma is increased by at least 0.01 U/mL,
   b) increases the maximal concentration of FVIII activity in plasma, or
   c) increases the area under the data curve (AUDC) of FVIII activity as compared to the respective parameter when the FVIII is administered in the same concentration, dose, and in the same mode of extravascular administration but without VWF.

3. The method according to claim 2, wherein the extravascular co-administration prolongs parameter a) by at least a factor of 3, increases parameter b) by at least a factor of 3, or increases parameter c) by at least a factor of 5 as compared to the respective parameter when the FVIII is administered in the same concentration, dose, and in the same mode of extravascular administration but without VWF.

4. A method for treating von Willebrand disease (VWD) and/or hemophilia A by generating fewer inhibitory antibodies against FVIII as compared to when the FVIII is administered in the same concentration, dose, and in the same mode of extravascular administration but without VWF comprising extravascularly co-administering von Willebrand factor (VWF) and factor VIII (FVIII), wherein the ratio of VWF antigen (VWF:Ag) to factor VIII-coagulant (FVIII:C) is larger than 5:1, wherein the VWF has a ratio of von Willebrand factor to ristocetin cofactor activity (VWF:RCoF) to von Willebrand factor antigen (VWF:Ag) which is equal to or less than 1:1.05, and wherein the VWF is not chemically modified.

5. The method according to claim 4, wherein the extravascular co-administration generates at least 15% fewer inhibitory antibodies as compared to when the pharmaceutical composition of FVIII is administered in the same concentration, dose, and in the same mode of extravascular administration but without VWF, and wherein the titer of inhibitory antibodies is determined with the Bethesda assay.

6. A method for treating von Willebrand disease (VWD) and/or hemophilia A, comprising extravascularly administering von Willebrand factor (VWF), wherein the VWF has a ratio of von Willebrand factor ristocetin cofactor activity (VWF:RCoF) to von Willebrand factor antigen (VWF:Ag) which is equal to or less than 1:1.05, and wherein the VWF is not chemically modified.

7. The method according to claim 1, wherein the von Willebrand factor is derived from human plasma or is produced recombinantly.

8. A method for treating von Willebrand disease (VWD) and/or hemophilia A, comprising extravascularly administering a composition comprising purified von Willebrand factor (VWF) and factor VIII (FVIII), wherein the ratio of VWF antigen (VWF:Ag) to factor VIII-coagulant (FVIII:C) is larger than 5:1, wherein the VWF has a ratio of von Willebrand factor to ristocetin cofactor activity (VWF:RCoF) to von Willebrand factor antigen (VWF:Ag) which is equal to or less than 1:1.05, wherein the VWF is not chemically modified, and wherein the von Willebrand factor is derived from human plasma or is produced recombinantly.

* * * * *